(12) United States Patent
Ando et al.

(10) Patent No.: US 8,420,718 B2
(45) Date of Patent: *Apr. 16, 2013

(54) COMPOSITION, POLYMERIZABLE COMPOSITION, RESIN, OPTICAL COMPONENT, AND METHOD FOR PRODUCING THE COMPOSITION

(75) Inventors: Tomoyuki Ando, Omuta (JP); Masakazu Murakami, Omuta (JP); Mamoru Takashina, Omuta (JP); Seiichi Kobayashi, Omuta (JP)

(73) Assignee: Mitsui Chemicals, Inc., Minato-Ku, Tokyo (JP)

(*) Notice: Subject to any disclaimer, the term of this patent is extended or adjusted under 35 U.S.C. 154(b) by 53 days.

This patent is subject to a terminal disclaimer.

(21) Appl. No.: 13/055,494

(22) PCT Filed: Jul. 23, 2009

(86) PCT No.: PCT/JP2009/003479
§ 371 (c)(1),
(2), (4) Date: Jan. 24, 2011

(87) PCT Pub. No.: WO2010/010713
PCT Pub. Date: Jan. 28, 2010

(65) Prior Publication Data
US 2011/0124836 A1 May 26, 2011

(30) Foreign Application Priority Data
Jul. 24, 2008 (JP) ................................. 2008-190456

(51) Int. Cl.
*C08K 5/00* (2006.01)
(52) U.S. Cl.
USPC ...... 524/83; 556/76; 528/77; 528/9; 528/375; 528/74

(58) Field of Classification Search .................... 524/83; 528/77, 9, 375, 374, 74; 556/76
See application file for complete search history.

(56) References Cited

U.S. PATENT DOCUMENTS

| 4,404,408 | A | 9/1983 | Wirth et al. |
| 5,670,441 | A | 9/1997 | Foedde et al. |
| 6,190,524 | B1 | 2/2001 | Kollah et al. |
| 6,348,121 | B1 | 2/2002 | Schoener et al. |
| 2007/0191615 | A1 | 8/2007 | Otsuji et al. |
| 2008/0027198 | A1 | 1/2008 | Naruse et al. |
| 2010/0179333 | A1 | 7/2010 | Otsuji et al. |
| 2010/0190949 | A1 | 7/2010 | Otsuji et al. |
| 2010/0261866 | A1 | 10/2010 | Naruse et al. |
| 2010/0298519 | A1 | 11/2010 | Nakamura et al. |

FOREIGN PATENT DOCUMENTS

| JP | 53-034730 A | 3/1978 |
| JP | 4-257558 A | 9/1992 |
| JP | 5-078308 A | 3/1993 |
| JP | 8-060046 A | 3/1996 |
| JP | 2003-327583 A | 11/2003 |
| WO | WO 2005/095490 A1 | 10/2005 |
| WO | WO 2006/054615 A1 | 5/2006 |
| WO | WO 2007/125636 A1 | 11/2007 |

OTHER PUBLICATIONS

International Search Report (PCT/ISA/210) for PCT/JP2009/003479 dated Oct. 27, 2009.
Office Action dated May 17, 2012, issued by the Chinese Patent Office in the corresponding Chinese Patent Application No. 200980126640.4. (5 pages).

*Primary Examiner* — Shane Fang
(74) *Attorney, Agent, or Firm* — Buchanan Ingersoll & Rooney PC

(57) ABSTRACT

The composition of the present invention contains a product having a thiol group obtained by reacting an Sb or Bi oxide or an Sb or Bi halide with at least one kind of polythiol compounds selected from compounds having at least two thiol groups in a molecule.

16 Claims, No Drawings

COMPOSITION, POLYMERIZABLE COMPOSITION, RESIN, OPTICAL COMPONENT, AND METHOD FOR PRODUCING THE COMPOSITION

TECHNICAL FIELD

The present invention relates to a composition, a polymerizable composition, a resin, an optical component, and a method for producing the composition.

BACKGROUND ART

In late years, a transparent organic polymer material has been used as a transparent material in place of an inorganic glass. When such a material is used, for example, for a resin for an optical, there has been demanded such a resin having required general properties such as transparency, thermal properties, mechanical properties and the like, while attaining a high refractive index.

A technique concerning such a resin has been disclosed in Patent Document 1. In the Document, a metal-containing thietane compound has been disclosed.

Patent Document 1: International Publication Pamphlet No. 2005/095490
Patent Document 2: Japanese Patent Laid-open No. 2003-327583
Patent Document 3: International Publication Pamphlet No. 2006/054615

DISCLOSURE OF THE INVENTION

However, there is room for improvement in view of enhancement of the refractive index in the aforementioned technique.

[1] A composition containing a product having a thiol group obtained by reacting an Sb or Bi oxide or an Sb or Bi halide with at least one kind of polythiol compounds selected from compounds having at least two thiol groups in a molecule.

[2] The composition as set forth in [1], wherein the polythiol compound is only composed of a carbon atom, a hydrogen atom and a sulfur atom.

[3] The composition as set forth in [2], wherein the polythiol compound is at least one kind of compounds selected from the group consisting of 1,2,3-propanetrithiol, 2,5-dimercapto-1,4-dithiane, 4-mercaptomethyl-1,8-dimercapto-3,6-dithiaoctane, 5,7-dimercaptomethyl-1,11-dimercapto-3,6,9-trithiaundecane, 4,7-dimercaptomethyl-1,11-dimercapto-3,6,9-trithiaundecane, 4,8-dimercaptomethyl-1,11-dimercapto-3,6,9-trithiaundecane, 1,1,3,3-tetrakis(mercaptomethylthio)propane, 4,6-bis(mercaptomethylthio)-1,3-dithiane and 2-(2,2-bis(mercaptomethylthio)ethyl)-1,3-dithietane.

[4] The composition as set forth in [3], wherein the polythiol compound is 4-mercaptomethyl-1,8-dimercapto-3,6-dithiaoctane.

[5] A polymerizable composition containing the composition as set forth in any one of [1] to [4], and at least one kind of compounds selected from the group consisting of an iso(thio)cyanate compound, an active hydrogen compound, an epoxy compound, an epithio compound and a thietane compound.

[6] A resin obtained by polymerizing the polymerizable composition as set forth in [5].

[7] An optical component composed of the resin as set forth in [6].

[8] A method for producing a composition containing a product having a thiol group synthesized by reacting an Sb or Bi oxide or an Sb or Bi halide with at least one kind of polythiol compounds selected from compounds having at least two thiol groups in a molecule.

According to the present invention, there is provided a composition which is capable of obtaining a transparent resin with an enhanced refractive index.

BEST MODE FOR CARRYING OUT THE INVENTION

Hereinafter, the present invention will be described using concrete embodiments, but the present invention is not restricted to these embodiments. Furthermore, in the present invention, for respective components and groups, exemplified compounds may be used singly or a plurality thereof may be used in combination. Furthermore, an organic group may contain a hetero atom other than a carbon atom and a hydrogen atom in the group. Concrete examples of the hetero atom include an oxygen atom, a sulfur atom and a nitrogen atom.

Initially, the composition of the present invention will be described.

The composition of the present invention contains a product having a thiol group obtained by reacting an Sb or Bi oxide or an Sb or Bi halide with at least one kind of polythiol compounds selected from compounds having at least two thiol groups in a molecule.

In particular, this composition is very excellent for use as an optical component.

By using such a composition, it is possible to obtain a transparent resin with an enhanced refractive index.

A metal compound to be a raw material of the aforementioned product is an Sb or Bi oxide or an Sb or Bi halide.

Examples of the Sb or Bi oxide include $Sb_2O_3$ and $Bi_2O_3$, while examples of the Sb or Bi halide include compounds represented by the following general formula (1), $$(Y)_{a-n}\text{-M-}(Z)_n \quad (1)$$

wherein, M represents Sb or Bi; Z represents a halogen atom; Y represents a monovalent inorganic or organic group; a represents a valence of M; and n represents an integer of not less than 1 and not more than a.

In particular, in view of handling such as stability and solubility of the raw material and/or product, it is preferable that a is n.

Examples of the halogen atom of Z include a fluorine atom, a chlorine atom, a bromine atom and an iodine atom.

Examples of Y include a hydrogen atom, an alkyl group, an aryl group, an alkyloxy group, an alkylthio group, an aryloxy group and an arylthio group. More concrete examples include a substituted or unsubstituted alkyl group, a substituted or unsubstituted aryl group, a substituted or unsubstituted alkyloxy group, a substituted or unsubstituted alkylthio group, a substituted or unsubstituted aryloxy group, and a substituted or unsubstituted arylthio group.

Concrete examples of the substituted or unsubstituted alkyl group include a straight chained alkyl group having 1 to 10 carbon atoms in total such as a methyl group, an ethyl group, an n-propyl group, an n-butyl group, an n-pentyl group, an n-hexyl group and the like;

a branched alkyl group having 3 to 10 carbon atoms in total such as an isopropyl group, an isobutyl group, a sec-butyl group, an isopentyl group, a sec-pentyl group, a 1-methylpentyl group, a 2-methylpentyl group, a 3-methylpentyl group, a 4-methylpentyl group, a 1-ethylbutyl group, a 2-ethylbutyl group, a 1-methylhexyl group, a 2-methylhexyl group, a 3-methylhexyl group, a 4-methylhexyl group, a 5-methylhexyl group, a 1-ethylpentyl group, a 2-ethylpentyl group, a 3-ethylpentyl group, a 1-n-propylbutyl group, a 1-iso-propylbutyl group, a 1-iso-propyl-2-methylpropyl group, a 1-methylheptyl group, a 2-methylheptyl group, a 3-methylheptyl group, a 4-methylheptyl group, a 5-methylheptyl group, a 6-methylheptyl group, a 1-ethylhexyl group, a 2-ethylhexyl group, a 3-ethylhexyl group, a 4-ethylhexyl group, a 1-n-propylpentyl group, a 2-n-propylpentyl group, a 1-iso-propylpentyl group, a 2-iso-propylpentyl group, a 1-n-butylbutyl group, a 1-iso-butylbutyl group, a 1-sec-butylbutyl group, a 1-tert-butylbutyl group, a 2-tert-butylbutyl group, a tert-butyl group, a tert-pentyl group, a 1,1-dimethylbutyl group, a 1,2-dimethylbutyl group, a 1,3-dimethylbutyl group, a 2,3-dimethylbutyl group, a 1-ethyl-2-methylpropyl group, a 1,1-dimethylpentyl group, a 1,2-dimethylpentyl group, a 1,3-dimethylpentyl group, a 1,4-dimethylpentyl group, a 2,2-dimethylpentyl group, a 2,3-dimethylpentyl group, a 2,4-dimethylpentyl group, a 3,3-dimethylpentyl group, a 3,4-dimethylpentyl group, a 1-ethyl-1-methylbutyl group, a 1-ethyl-2-methylbutyl group, a 1-ethyl-3-methylbutyl group, a 2-ethyl-1-methylbutyl group, a 2-ethyl-3-methylbutyl group, a 1,1-dimethylhexyl group, a 1,2-dimethylhexyl group, a 1,3-dimethylhexyl group, a 1,4-dimethylhexyl group, a 1,5-dimethylhexyl group, a 2,2-dimethylhexyl group, a 2,3-dimethylhexyl group, a 2,4-dimethylhexyl group, a 2,5-dimethylhexyl group, a 3,3-dimethylhexyl group, a 3,4-dimethylhexyl group, a 3,5-dimethylhexyl group, a 4,4-dimethylhexyl group, a 4,5-dimethylhexyl group, a 1-ethyl-2-methylpentyl group, a 1-ethyl-3-methylpentyl group, a 1-ethyl-4-methylpentyl group, a 2-ethyl-1-methylpentyl group, a 2-ethyl-2-methylpentyl group, a 2-ethyl-3-methylpentyl group, a 2-ethyl-4-methylpentyl group, a 3-ethyl-1-methylpentyl group, a 3-ethyl-2-methylpentyl group, a 3-ethyl-3-methylpentyl group, a 3-ethyl-4-methylpentyl group, a 1-n-propyl-1-methylbutyl group, a 1-n-propyl-2-methylbutyl group, a 1-n-propyl-3-methylbutyl group, a 1-iso-propyl-1-methylbutyl group, a 1-iso-propyl-2-methylbutyl group, a 1-iso-propyl-3-methylbutyl group, a 1,1-diethylbutyl group, a 1,2-diethylbutyl group, a 1,1,2-trimethylpropyl group, a 1,2,2-trimethylpropyl group, a 1,1,2-trimethylbutyl group, a 1,1,3-trimethylbutyl group, a 1,2,3-trimethylbutyl group, a 1,2,2-trimethylbutyl group, a 1,3,3-trimethylbutyl group, a 2,3,3-trimethylbutyl group, a 1,1,2-trimethylpentyl group, a 1,1,3-trimethylpentyl group, a 1,1,4-trimethylpentyl group, a 1,2,2-trimethylpentyl group, a 1,2,3-trimethylpentyl group, a 1,2,4-trimethylpentyl group, a 1,3,4-trimethylpentyl group, a 2,2,3-trimethylpentyl group, a 2,2,4-trimethylpentyl group, a 2,3,4-trimethylpentyl group, a 1,3,3-trimethylpentyl group, a 2,3,3-trimethylpentyl group, a 3,3,4-trimethylpentyl group, a 1,4,4-trimethylpentyl group, a 2,4,4-trimethylpentyl group, a 3,4,4-trimethylpentyl group, a 1-ethyl-1,2-dimethylbutyl group, a 1-ethyl-1,3-dimethylbutyl group, a 1-ethyl-2,3-dimethylbutyl group, a 2-ethyl-1,1-dimethylbutyl group, a 2-ethyl-1,2-dimethylbutyl group, a 2-ethyl-1,3-dimethylbutyl group, a 2-ethyl-2,3-dimethylbutyl group and the like; and a saturated cyclic alkyl group having 5 to 10 carbon atoms in total such as a cyclopentyl group, a cyclohexyl group, a methylcyclopentyl group, a methoxycyclopentyl group, a methoxycyclohexyl group, a methylcyclohexyl group, a 1,2-dimethylcyclohexyl group, a 1,3-dimethylcyclohexyl group, a 1,4-dimethylcyclohexyl group, an ethylcyclohexyl group and the like.

Concrete examples of the substituted or unsubstituted aryl group include aromatic hydrocarbon having not more than 20 carbon atoms in total such as a phenyl group, a naphthyl group, an anthranyl group, a cyclopentadienyl group and the like;

an alkyl-substituted aryl group having not more than 20 carbon atoms in total such as a 2-methylphenyl group, a 3-methylphenyl group, a 4-methylphenyl group, a 2-ethylphenyl group, a propylphenyl group, a butylphenyl group, a hexylphenyl group, a cyclohexylphenyl group, an octylphenyl group, a 2-methyl-1-naphthyl group, a 3-methyl-1-naphthyl group, a 4-methyl-1-naphthyl group, a 5-methyl-1-naphthyl group, a 6-methyl-1-naphthyl group, a 7-methyl-1-naphthyl group, a 8-methyl-1-naphthyl group, a 1-methyl-2-naphthyl group, a 3-methyl-2-naphthyl group, a 4-methyl-2-naphthyl group, a 5-methyl-2-naphthyl group, a 6-methyl-2-naphthyl group, a 7-methyl-2-naphthyl group, a 8-methyl-2-naphthyl group, a 2-ethyl-1-naphthyl group, a 2,3-dimethylphenyl group, a 2,4-dimethylphenyl group, a 2,5-dimethylphenyl group, a 2,6-dimethylphenyl group, a 3,4-dimethylphenyl group, a 3,5-dimethylphenyl group, a 3,6-dimethylphenyl group, a 2,3,4-trimethylphenyl group, a 2,3,5-trimethylphenyl group, a 2,3,6-trimethylphenyl group, a 2,4,5-trimethylphenyl group, a 2,4,6-trimethylphenyl group, a 3,4,5-trimethylphenyl group and the like;

a monoalkoxyaryl group having not more than 20 carbon atoms in total wherein a substituted or unsubstituted alkyloxy group having not more than 10 carbon atoms is substituted, such as a 2-methoxyphenyl group, a 3-methoxyphenyl group, a 4-methoxyphenyl group, a 2-ethoxyphenyl group, a propoxyphenyl group, a butoxyphenyl group, a hexyloxyphenyl group, a cyclohexyloxyphenyl group, an octyloxyphenyl group, a 2-methoxy-1-naphthyl group, a 3-methoxy-1-naphthyl group, a 4-methoxy-1-naphthyl group, a 5-methoxy-1-naphthyl group, a 6-methoxy-1-naphthyl group, a 7-methoxy-1-naphthyl group, a 8-methoxy-1-naphthyl group, a 1-methoxy-2-naphthyl group, a 3-methoxy-2-naphthyl group, a 4-methoxy-2-naphthyl group, a 5-methoxy-2-naphthyl group, a 6-methoxy-2-naphthyl group, a 7-methoxy-2-naphthyl group, a 8-methoxy-2-naphthyl group, a 2-ethoxy-1-naphthyl group and the like;

a dialkoxyaryl group having not more than 20 carbon atoms in total wherein a substituted or unsubstituted alkyloxy group having not more than 10 carbon atoms is substituted, such as a 2,3-dimethoxyphenyl group, a 2,4-dimethoxyphenyl group, a 2,5-dimethoxyphenyl group, a 2,6-dimethoxyphenyl group, a 3,4-dimethoxyphenyl group, a 3,5-dimethoxyphenyl group, a 3,6-dimethoxyphenyl group, a 4,5-dimethoxy-1-naphthyl group, a 4,7-dimethoxy-1-naphthyl group, a 4,8-dimethoxy-1-naphthyl group, a 5,8-dimethoxy-1-naphthyl group, a 5,8-dimethoxy-2-naphthyl group and the like;

a trialkoxyaryl group having not more than 20 carbon atoms in total wherein a substituted or unsubstituted alkyloxy group having not more than 10 carbon atoms is substituted, such as a 2,3,4-trimethoxyphenyl group, a 2,3,5-trimethoxyphenyl group, a 2,3,6-trimethoxyphenyl group, a 2,4,5-trimethoxyphenyl group, a 2,4,6-trimethoxyphenyl group, a 3,4,5-trimethoxyphenyl group and the like; and an aryl group having not more than 20 carbon atoms in total wherein a halogen atom is substituted, such as a chlorophenyl group, a dichlorophenyl group, a trichlorophenyl group, a bromophenyl group, a dibromophenyl group, an iodophenyl group, a fluorophenyl group, a chloronaphthyl group, a bromonaphthyl group, a difluorophenyl group, a trifluorophenyl group, a tetrafluorophenyl group, a pentafluorophenyl group and the like.

Concrete examples of the substituted or unsubstituted alkyloxy group include a straight chained or branched alkoxy group having 1 to 10 carbon atoms in total such as a methoxy group, an ethoxy group, an n-propoxy group, an iso-propoxy group, an n-butoxy group, an iso-butoxy group, a tert-butoxy group, an n-pentyloxy group, an iso-pentyloxy group, an n-hexyloxy group, an iso-hexyloxy group, a 2-ethylhexyloxy group, a 3,5,5-trimethylhexyloxy group, an n-heptyloxy group, an n-octyloxy group, an n-nonyloxy group and the like;

a cycloalkoxy group having 5 to 10 carbon atoms in total such as a cyclopentyloxy group, a cyclohexyloxy group and the like;

an alkoxyalkoxy group having 1 to 10 carbon atoms in total such as a methoxymethoxy group, an ethoxymethoxy group, an ethoxyethoxy group, an n-propoxymethoxy group, an iso-propoxymethoxy group, an n-propoxyethoxy group, an iso-propoxyethoxy group, an n-butoxyethoxy group, an iso-butoxyethoxy group, a tert-butoxyethoxy group, an n-pentyloxyethoxy group, an iso-pentyloxyethoxy group, an n-hexyloxyethoxy group, an iso-hexyloxyethoxy group, an n-heptyloxyethoxy group and the like; and an aralkyloxy group such as a benzyloxy group and the like.

Concrete examples of the substituted or unsubstituted alkylthio group include a straight chained or branched alkylthio group having 1 to 10 carbon atoms in total such as a methylthio group, an ethylthio group, an n-propylthio group, an i-propylthio group, an n-butylthio group, an i-butylthio group, a sec-butylthio group, a t-butylthio group, an n-pentylthio group, an iso-pentylthio group, an n-hexylthio group, an iso-hexylthio group, a 2-ethylhexylthio group, a 3,5,5-trimethylhexylthio group, an n-heptylthio group, an n-octylthio group, an n-nonylthio group and the like;

a cycloalkylthio group having 5 to 10 carbon atoms in total such as a cyclopentylthio group, a cyclohexylthio group and the like;

an alkoxyalkylthio group having 1 to 10 carbon atoms in total such as a methoxyethylthio group, an ethoxyethylthio group, an n-propoxyethylthio group, an iso-propoxyethylthio group, an n-butoxyethylthio group, an iso-butoxyethylthio group, a tert-butoxyethylthio group, an n-pentyloxyethylthio group, an iso-pentyloxyethylthio group, an n-hexyloxyethylthio group, an iso-hexyloxyethylthio group, an n-heptyloxyethylthio group and the like;

an aralkylthio group such as a benzylthio group and the like; and an alkylthioalkylthio group having 1 to 10 carbon atoms in total such as a methylthioethylthio group, an ethylthioethylthio group, an n-propylthioethylthio group, an iso-propylthioethylthio group, an n-butylthioethylthio group, an iso-butylthioethylthio group, a tert-butylthioethylthio group, an n-pentylthioethylthio group, an iso-pentylthioethylthio group, an n-hexylthioethylthio group, an iso-hexylthioethylthio group, an n-heptylthioethylthio group and the like.

Concrete examples of the substituted or unsubstituted aryloxy group include an unsubstituted or alkyl-substituted aryloxy group having not more than 20 carbon atoms in total such as a phenyloxy group, a naphthyloxy group, an anthranyloxy group, a 2-methylphenyloxy group, a 3-methylphenyloxy group, a 4-methylphenyloxy group, a 2-ethylphenyloxy group, a propylphenyloxy group, a butylphenyloxy group, a hexylphenyloxy group, a cyclohexylphenyloxy group, an octylphenyloxy group, a 2-methyl-1-naphthyloxy group, a 3-methyl-1-naphthyloxy group, a 4-methyl-1-naphthyloxy group, a 5-methyl-1-naphthyloxy group, a 6-methyl-1-naphthyloxy group, a 7-methyl-1-naphthyloxy group, a 8-methyl-1-naphthyloxy group, a 1-methyl-2-naphthyloxy group, a 3-methyl-2-naphthyloxy group, a 4-methyl-2-naphthyloxy group, a 5-methyl-2-naphthyloxy group, a 6-methyl-2-naphthyloxy group, a 7-methyl-2-naphthyloxy group, a 8-methyl-2-naphthyloxy group, a 2-ethyl-1-naphthyloxy group, a 2,3-dimethylphenyloxy group, a 2,4-dimethylphenyloxy group, a 2,5-dimethylphenyloxy group, a 2,6-dimethylphenyloxy group, a 3,4-dimethylphenyloxy group, a 3,5-dimethylphenyloxy group, a 3,6-dimethylphenyloxy group, a 2,3,4-trimethylphenyloxy group, a 2,3,5-trimethylphenyloxy group, a 2,3,6-trimethylphenyloxy group, a 2,4,5-trimethylphenyloxy group, a 2,4,6-trimethylphenyloxy group, a 3,4,5-trimethylphenyloxy group and the like;

a monoalkoxyaryloxy group having not more than 20 carbon atoms in total wherein a substituted or unsubstituted alkyloxy group having not more than 10 carbon atoms is substituted, such as a 2-methoxyphenyloxy group, a 3-methoxyphenyloxy group, a 4-methoxyphenyloxy group, a 2-ethoxyphenyloxy group, a propoxyphenyloxy group, a butoxyphenyloxy group, a hexyloxyphenyloxy group, a cyclohexyloxyphenyloxy group, an octyloxyphenyloxy group, a 2-methoxy-1-naphthyloxy group, a 3-methoxy-1-naphthyloxy group, a 4-methoxy-1-naphthyloxy group, a 5-methoxy-1-naphthyloxy group, a 6-methoxy-1-naphthyloxy group, a 7-methoxy-1-naphthyloxy group, a 8-methoxy-1-naphthyloxy group, a 1-methoxy-2-naphthyloxy group, a 3-methoxy-2-naphthyloxy group, a 4-methoxy-2-naphthyloxy group, a 5-methoxy-2-naphthyloxy group, a 6-methoxy-2-naphthyloxy group, a 7-methoxy-2-naphthyloxy group, a 8-methoxy-2-naphthyloxy group, a 2-ethoxy-1-naphthyloxy group and the like;

a dialkoxyaryloxy group having not more than 20 carbon atoms in total wherein a substituted or unsubstituted alkyloxy group having not more than 10 carbon atoms is substituted, such as a 2,3-dimethoxyphenyloxy group, a 2,4-dimethoxyphenyloxy group, a 2,5-dimethoxyphenyloxy group, a 2,6-dimethoxyphenyloxy group, a 3,4-dimethoxyphenyloxy group, a 3,5-dimethoxyphenyloxy group, a 3,6-dimethoxyphenyloxy group, a 4,5-dimethoxy-1-naphthyloxy group, a 4,7-dimethoxy-1-naphthyloxy group, a 4,8-dimethoxy-1-naphthyloxy group, a 5,8-dimethoxy-1-naphthyloxy group, a 5,8-dimethoxy-2-naphthyloxy group and the like;

a trialkoxyaryloxy group having not more than 20 carbon atoms in total wherein a substituted or unsubstituted alkyloxy group having not more than 10 carbon atoms is substituted, such as a 2,3,4-trimethoxyphenyloxy group, a 2,3,5-trimethoxyphenyloxy group, a 2,3,6-trimethoxyphenyloxy group, a 2,4,5-trimethoxyphenyloxy group, a 2,4,6-trimethoxyphenyloxy group, a 3,4,5-trimethoxyphenyloxy group and the like; and an aryloxy group having not more than 20 carbon atoms in total wherein a halogen atom is substituted, such as a chlorophenyloxy group, a dichlorophenyloxy group, a trichlorophenyloxy group, a bromophenyloxy group, a dibromophenyloxy group, an iodophenyloxy group, a fluorophenyloxy group, a chloronaphthyloxy group, a bromonaphthyloxy group, a difluorophenyloxy group, a trifluorophenyloxy group, a tetrafluorophenyloxy group, a pentafluorophenyloxy group and the like.

Concrete examples of the substituted or unsubstituted arylthio group include an unsubstituted or alkyl-substituted arylthio group having not more than 20 carbon atoms in total such as a phenylthio group, a naphthylthio group, an anthranylthio group, a 2-methylphenylthio group, a 3-methylphenylthio group, a 4-methylphenylthio group, a 2-ethylphenylthio group, a propylphenylthio group, a butylphenylthio group, a hexylphenylthio group, a cyclohexylphenylthio group, an octylphenylthio group, a 2-methyl-1-naphthylthio group, a 3-methyl-1-naphthylthio group, a 4-methyl-1-naphthylthio group, a 5-methyl-1-naphthylthio group, a 6-methyl-1-naphthylthio group, a 7-methyl-1-naphthylthio group, a 8-methyl-1-naphthylthio group, a 1-methyl-2-naphthylthio group, a 3-methyl-2-naphthylthio group, a 4-methyl-2-naphthylthio group, a 5-methyl-2-naphthylthio group, a 6-methyl-2-naphthylthio group, a 7-methyl-2-naphthylthio group, a 8-methyl-2-naphthylthio group, a 2-ethyl-1-naphthylthio group, a 2,3-dimethylphenylthio group, a 2,4-dimethylphenylthio group, a 2,5-dimethylphenylthio group, a 2,6-dimethylphenylthio group, a 3,4-dimethylphenylthio group, a 3,5-dimethylphenylthio group, a 3,6-dimethylphenylthio group, a 2,3,4-trimethylphenylthio group, a 2,3,5-trimethylphenylthio group, a 2,3,6-trimethylphenylthio group, a 2,4,5-trimethylphenylthio group, a 2,4,6-trimethylphenylthio group, a 3,4,5-trimethylphenylthio group and the like;

a monoalkoxyarylthio group having not more than 20 carbon atoms in total wherein a substituted or unsubstituted alkyloxy group having not more than 10 carbon atoms is substituted, such as a 2-methoxyphenylthio group, a 3-methoxyphenylthio group, a 4-methoxyphenylthio group, a 2-ethoxyphenylthio group, a propoxyphenylthio group, a butoxyphenylthio group, a hexyloxyphenylthio group, a cyclohexyloxyphenylthio group, an octyloxyphenylthio group, a 2-methoxy-1-naphthylthio group, a 3-methoxy-1-naphthylthio group, a 4-methoxy-1-naphthylthio group, a 5-methoxy-1-naphthylthio group, a 6-methoxy-1-naphthylthio group, a 7-methoxy-1-naphthylthio group, a 8-methoxy-1-naphthylthio group, a 1-methoxy-2-naphthylthio group, a 3-methoxy-2-naphthylthio group, a 4-methoxy-2-naphthylthio group, a 5-methoxy-2-naphthylthio group, a 6-methoxy-2-naphthylthio group, a 7-methoxy-2-naphthylthio group, a 8-methoxy-2-naphthylthio group, a 2-ethoxy-1-naphthylthio group and the like;

a dialkoxyarylthio group having not more than 20 carbon atoms in total wherein a substituted or unsubstituted alkyloxy group having not more than 10 carbon atoms is substituted, such as a 2,3-dimethoxyphenylthio group, a 2,4-dimethoxyphenylthio group, a 2,5-dimethoxyphenylthio group, a 2,6-dimethoxyphenylthio group, a 3,4-dimethoxyphenylthio group, a 3,5-dimethoxyphenylthio group, a 3,6-dimethoxyphenylthio group, a 4,5-dimethoxy-1-naphthylthio group, a 4,7-dimethoxy-1-naphthylthio group, a 4,8-dimethoxy-1-naphthylthio group, a 5,8-dimethoxy-1-naphthylthio group, a 5,8-dimethoxy-2-naphthylthio group and the like;

a trialkoxyarylthio group having not more than 20 carbon atoms in total wherein a substituted or unsubstituted alkyloxy group having not more than 10 carbon atoms is substituted, such as a 2,3,4-trimethoxyphenylthio group, a 2,3,5-trimethoxyphenylthio group, a 2,3,6-trimethoxyphenylthio group, a 2,4,5-trimethoxyphenylthio group, a 2,4,6-trimethoxyphenylthio group, a 3,4,5-trimethoxyphenylthio group and the like; and an arylthio group having not more than 20 carbon atoms in total wherein a halogen atom is substituted, such as a chlorophenylthio group, a dichlorophenylthio group, a trichlorophenylthio group, a bromophenylthio group, a dibromophenylthio group, an iodophenylthio group, a fluorophenylthio group, a chloronaphthylthio group, a bromonaphthylthio group, a difluorophenylthio group, a trifluorophenylthio group, a tetrafluorophenylthio group, a pentafluorophenylthio group and the like, but are not restricted to these exemplified compounds alone.

A preferable example of Y includes a hydrogen atom.

Preferable examples of the substituted or unsubstituted alkyl group include a straight chained alkyl group having 1 to 6 carbon atoms in total such as a methyl group, an ethyl group, an n-propyl group, an n-butyl group, an n-pentyl group, an n-hexyl group and the like;

a branched alkyl group having 3 to 6 carbon atoms in total such as an isopropyl group, an isobutyl group, a sec-butyl group, an isopentyl group, a sec-pentyl group, a 1-methylpentyl group, a 2-methylpentyl group, a 3-methylpentyl group, a 4-methylpentyl group, a 1-ethylbutyl group, a 2-ethylbutyl group, a tert-butyl group, a tert-pentyl group, a 1,1-dimethylbutyl group, a 1,2-dimethylbutyl group, a 1,3-dimethylbutyl group, a 2,3-dimethylbutyl group and the like; and a saturated cyclic alkyl group having 5 to 6 carbon atoms in total such as a cyclopentyl group, a cyclohexyl group and the like.

Preferable examples of the substituted or unsubstituted aryl group include aromatic hydrocarbon having not more than 12 carbon atoms in total such as a phenyl group, a naphthyl group, a cyclopentadienyl group and the like;

an alkyl-substituted aryl group having not more than 12 carbon atoms in total such as a 2-methylphenyl group, a 3-methylphenyl group, a 4-methylphenyl group, a 2-ethylphenyl group, a propylphenyl group, a butylphenyl group, a 2,3-dimethylphenyl group, a 2,4-dimethylphenyl group, a 2,5-dimethylphenyl group, a 2,6-dimethylphenyl group, a 3,4-dimethylphenyl group, a 3,5-dimethylphenyl group, a 3,6-dimethylphenyl group, a 2,3,4-trimethylphenyl group, a 2,3,5-trimethylphenyl group, a 2,3,6-trimethylphenyl group, a 2,4,5-trimethylphenyl group, a 2,4,6-trimethylphenyl group, a 3,4,5-trimethylphenyl group and the like;

a monoalkoxyaryl group having not more than 12 carbon atoms in total wherein a substituted or unsubstituted alkyloxy group having not more than 6 carbon atoms is substituted, such as a 2-methoxyphenyl group, a 3-methoxyphenyl group, a 4-methoxyphenyl group, a 2-ethoxyphenyl group, a propoxyphenyl group, a butoxyphenyl group and the like;

a dialkoxyaryl group having not more than 12 carbon atoms in total wherein a substituted or unsubstituted alkyloxy group having not more than 6 carbon atoms is substituted, such as a 2,3-dimethoxyphenyl group, a 2,4-dimethoxyphenyl group, a 2,5-dimethoxyphenyl group, a 2,6-dimethoxyphenyl group, a 3,4-dimethoxyphenyl group, a 3,5-dimethoxyphenyl group, a 3,6-dimethoxyphenyl group and the like; and an aryl group having not more than 12 carbon atoms in total wherein a halogen atom is substituted, such as a chlorophenyl group, a dichlorophenyl group, a trichlorophenyl group, a bromophenyl group, a dibromophenyl group, an iodophenyl group, a fluorophenyl group, a chloronaphthyl group, a bromonaphthyl group, a difluorophenyl group, a trifluorophenyl group, a tetrafluorophenyl group, a pentafluorophenyl group and the like.

Preferable examples of the substituted or unsubstituted alkyloxy group include a straight chained or branched alkoxy group having 1 to 6 carbon atoms in total such as a methoxy group, an ethoxy group, an n-propoxy group, an iso-propoxy group, an n-butoxy group, an iso-butoxy group, a tert-butoxy group, an n-pentyloxy group, an iso-pentyloxy group, an n-hexyloxy group, an iso-hexyloxy group and the like;

a cycloalkoxy group having 5 to 6 carbon atoms in total such as a cyclopentyloxy group, a cyclohexyloxy group and the like; and an alkoxyalkoxy group having 1 to 6 carbon atoms in total such as a methoxymethoxy group, an ethoxymethoxy group, an ethoxyethoxy group, an n-propoxymethoxy group, an iso-propoxymethoxy group, an n-propoxyethoxy group, an iso-propoxyethoxy group, an n-butoxyethoxy group, an iso-butoxyethoxy group, a tert-butoxyethoxy group and the like.

Preferable examples of the substituted or unsubstituted alkylthio group include a straight chained or branched alkylthio group having 1 to 6 carbon atoms in total such as a methylthio group, an ethylthio group, an n-propylthio group, an i-propylthio group, an n-butylthio group, an i-butylthio group, a sec-butylthio group, a t-butylthio group, an n-pentylthio group, an iso-pentylthio group, an n-hexylthio group, an iso-hexylthio group and the like;

a cycloalkylthio group having 5 to 6 carbon atoms in total such as a cyclopentylthio group, a cyclohexylthio group and the like;

an alkoxyalkylthio group having 1 to 6 carbon atoms in total such as a methoxyethylthio group, an ethoxyethylthio group, an n-propoxyethylthio group, an iso-propoxyethylthio group, an n-butoxyethylthio group, an iso-butoxyethylthio group, a tert-butoxyethylthio group and the like; and an alkylthioalkylthio group having 1 to 6 carbon atoms in total such as a methylthioethylthio group, an ethylthioethylthio group, an n-propylthioethylthio group, an iso-propylthioethylthio group, an n-butylthioethylthio group, an iso-butylthioethylthio group, a tert-butylthioethylthio group and the like.

Preferable examples of the substituted or unsubstituted aryloxy group include an unsubstituted or alkyl-substituted aryloxy group having not more than 12 carbon atoms in total such as a phenyloxy group, a naphthyloxy group, a 2-methylphenyloxy group, a 3-methylphenyloxy group, a 4-methylphenyloxy group, a 2-ethylphenyloxy group, a propylphenyloxy group, a butylphenyloxy group, a hexylphenyloxy group, a cyclohexylphenyloxy group, a 2,4-dimethylphenyloxy group, a 2,5-dimethylphenyloxy group, a 2,6-dimethylphenyloxy group, a 3,4-dimethylphenyloxy group, a 3,5-dimethylphenyloxy group, a 3,6-dimethylphenyloxy group, a 2,3,4-trimethylphenyloxy group, a 2,3,5-trimethylphenyloxy group, a 2,3,6-trimethylphenyloxy group, a 2,4,5-trimethylphenyloxy group, a 2,4,6-trimethylphenyloxy group, a 3,4,5-trimethylphenyloxy group and the like;

a monoalkoxyaryloxy group having not more than 12 carbon atoms in total wherein a substituted or unsubstituted alkyloxy group having not more than 6 carbon atoms is substituted, such as a 2-methoxyphenyloxy group, a 3-methoxyphenyloxy group, a 4-methoxyphenyloxy group, a 2-ethoxyphenyloxy group, a propoxyphenyloxy group, a butoxyphenyloxy group, a hexyloxyphenyloxy group, a cyclohexyloxyphenyloxy group and the like;

a dialkoxyaryloxy group having not more than 12 carbon atoms in total wherein a substituted or unsubstituted alkyloxy group having not more than 6 carbon atoms is substituted, such as a 2,3-dimethoxyphenyloxy group, a 2,4-dimethoxyphenyloxy group, a 2,5-dimethoxyphenyloxy group, a 2,6-dimethoxyphenyloxy group, a 3,4-dimethoxyphenyloxy group, a 3,5-dimethoxyphenyloxy group, a 3,6-dimethoxyphenyloxy group and the like; and an aryloxy group having not more than 12 carbon atoms in total wherein a halogen atom is substituted, such as a chlorophenyloxy group, a dichlorophenyloxy group, a trichlorophenyloxy group, a bromophenyloxy group, a dibromophenyloxy group, an iodophenyloxy group, a fluorophenyloxy group, a chloronaphthyloxy group, a bromonaphthyloxy group, a difluorophenyloxy group, a trifluorophenyloxy group, a tetrafluorophenyloxy group, a pentafluorophenyloxy group and the like.

Preferable examples of the substituted or unsubstituted arylthio group include an unsubstituted or alkyl-substituted arylthio group having not more than 12 carbon atoms in total such as a phenylthio group, a naphthylthio group, a 2-methylphenylthio group, a 3-methylphenylthio group, a 4-methylphenylthio group, a 2-ethylphenylthio group, a propylphenylthio group, a butylphenylthio group, a hexylphenylthio group, a cyclohexylphenylthio group, a 2,4-dimethylphenylthio group, a 2,5-dimethylphenylthio group, a 2,6-dimethylphenylthio group, a 3,4-dimethylphenylthio group, a 3,5-dimethylphenylthio group, a 3,6-dimethylphenylthio group, a 2,3,4-trimethylphenylthio group, a 2,3,5-trimethylphenylthio group, a 2,3,6-trimethylphenylthio group, a 2,4,5-trimethylphenylthio group, a 2,4,6-trimethylphenylthio group, a 3,4,5-trimethylphenylthio group and the like;

a monoalkoxyarylthio group having not more than 12 carbon atoms in total wherein a substituted or unsubstituted alkyloxy group having not more than 6 carbon atoms is substituted, such as a 2-methoxyphenylthio group, a 3-methoxyphenylthio group, a 4-methoxyphenylthio group, a 2-ethoxyphenylthio group, a propoxyphenylthio group, a butoxyphenylthio group, a hexyloxyphenylthio group, a cyclohexyloxyphenylthio group and the like;

a dialkoxyarylthio group having not more than 12 carbon atoms in total wherein a substituted or unsubstituted alkyloxy group having not more than 6 carbon atoms is substituted, such as a 2,3-dimethoxyphenylthio group, a 2,4-dimethoxyphenylthio group, a 2,5-dimethoxyphenylthio group, a 2,6-dimethoxyphenylthio group, a 3,4-dimethoxyphenylthio group, a 3,5-dimethoxyphenylthio group, a 3,6-dimethoxyphenylthio group, a 4,5-dimethoxy-1-naphthylthio group, a 4,7-dimethoxy-1-naphthylthio group, a 4,8-dimethoxy-1-naphthylthio group, a 5,8-dimethoxy-1-naphthylthio group, a 5,8-dimethoxy-2-naphthylthio group and the like; and an arylthio group having not more than 12 carbon atoms in total wherein a halogen atom is substituted, such as a chlorophenylthio group, a dichlorophenylthio group, a trichlorophenylthio group, a bromophenylthio group, a dibromophenylthio group, an iodophenylthio group, a fluorophenylthio group, a chloronaphthylthio group, a bromonaphthylthio group, a difluorophenylthio group, a trifluorophenylthio group, a tetrafluorophenylthio group, a pentafluorophenylthio group and the like.

A more preferable example of Y includes a hydrogen atom.

More preferable examples of the substituted or unsubstituted alkyl group include a straight chained or branched alkyl group having 1 to 3 carbon atoms in total such as a methyl group, an ethyl group, an iso-propyl group and the like.

More preferable examples of the substituted or unsubstituted aryl group include aromatic hydrocarbon having not more than 12 carbon atoms in total such as a phenyl group, a naphthyl group, a cyclopentadienyl group and the like;

an alkyl-substituted aryl group having not more than 9 carbon atoms in total such as a 2-methylphenyl group, a 3-methylphenyl group, a 4-methylphenyl group, a 2-ethylphenyl group, a propylphenyl group, a 2,3-dimethylphenyl group, a 2,4-dimethylphenyl group, a 2,5-dimethylphenyl group, a 2,6-dimethylphenyl group, a 3,4-dimethylphenyl group, a 3,5-dimethylphenyl group, a 3,6-dimethylphenyl group and the like;

a monoalkoxyaryl group having not more than 9 carbon atoms in total wherein a substituted or unsubstituted alkyloxy group having not more than 3 carbon atoms is substituted, such as a 2-methoxyphenyl group, a 3-methoxyphenyl group, a 4-methoxyphenyl group, a 2-ethoxyphenyl group, a propoxyphenyl group and the like; and an aryl group having not more than 12 carbon atoms in total wherein a halogen atom is substituted, such as a chlorophenyl group, a dichlorophenyl group, a trichlorophenyl group, a bromophenyl group, a dibromophenyl group, a chloronaphthyl group, a bromonaphthyl group and the like.

More preferable examples of the substituted or unsubstituted alkyloxy group include a straight chained or branched alkoxy group having 1 to 3 carbon atoms in total such as a methoxy group, an ethoxy group, an iso-propoxy group and the like; and a cycloalkoxy group having 5 to 6 carbon atoms in total such as a cyclopentyloxy group, a cyclohexyloxy group and the like.

More preferable examples of the substituted or unsubstituted alkylthio group include a straight chained or branched alkylthio group having 1 to 3 carbon atoms in total such as a methylthio group, an ethylthio group, an n-propylthio group, an i-propylthio group and the like;

a cycloalkylthio group having 5 to 6 carbon atoms in total such as a cyclopentylthio group, a cyclohexylthio group and the like; and an alkylthioalkylthio group having 1 to 6 carbon atoms in total such as a methylthioethylthio group, an ethylthioethylthio group, an n-propylthioethylthio group, an iso-propylthioethylthio group, an n-butylthioethylthio group, an iso-butylthioethylthio group, a tert-butylthioethylthio group and the like.

More preferable examples of the substituted or unsubstituted aryloxy group include an unsubstituted or alkyl-substituted aryloxy group having not more than 9 carbon atoms in total such as a phenyloxy group, a naphthyloxy group, a 2-methylphenyloxy group, a 3-methylphenyloxy group, a 4-methylphenyloxy group, a 2-ethylphenyloxy group, a propylphenyloxy group, a 2,4-dimethylphenyloxy group, a 2,5-dimethylphenyloxy group, a 2,6-dimethylphenyloxy group, a 3,4-dimethylphenyloxy group, a 3,5-dimethylphenyloxy group, a 3,6-dimethylphenyloxy group and the like;

a monoalkoxyaryloxy group having not more than 9 carbon atoms in total wherein a substituted or unsubstituted alkyloxy group having not more than 3 carbon atoms is substituted, such as a 2-methoxyphenyloxy group, a 3-methoxyphenyloxy group, a 4-methoxyphenyloxy group, a 2-ethoxyphenyloxy group, a propoxyphenyloxy group and the like; and an aryloxy group having not more than 12 carbon atoms in total wherein a halogen atom is substituted, such as a chlorophenyloxy group, a dichlorophenyloxy group, a trichlorophenyloxy group, a bromophenyloxy group, a dibromophenyloxy group, a chloronaphthyloxy group, a bromonaphthyloxy group and the like.

More preferable examples of the substituted or unsubstituted arylthio group include an unsubstituted or alkyl-substituted arylthio group having not more than 9 carbon atoms in total such as a phenylthio group, a 2-methylphenylthio group, a 3-methylphenylthio group, a 4-methylphenylthio group, a 2-ethylphenylthio group, a propylphenylthio group, a 2,4-dimethylphenylthio group, a 2,5-dimethylphenylthio group, a 2,6-dimethylphenylthio group, a 3,4-dimethylphenylthio group, a 3,5-dimethylphenylthio group, a 3,6-dimethylphenylthio group and the like;

a monoalkoxyarylthio group having not more than 9 carbon atoms in total wherein a substituted or unsubstituted alkyloxy group having not more than 3 carbon atoms is substituted, such as a 2-methoxyphenylthio group, a 3-methoxyphenylthio group, a 4-methoxyphenylthio group, a 2-ethoxyphenylthio group, a propoxyphenylthio group and the like; and an arylthio group having not more than 12 carbon atoms in total wherein a halogen atom is substituted, such as a chlorophenylthio group, a dichlorophenylthio group, a trichlorophenylthio group, a bromophenylthio group, a dibromophenylthio group, a chloronaphthylthio group, a bromonaphthylthio group and the like.

Next, the polythiol compound having at least two thiol groups in a molecule will be described.

The polythiol compound having at least two thiol groups in a molecule is an aliphatic polythiol compound such as 1,2-ethanedithiol, 1,2,3-propanetrithiol and the like, or a polythiol compound having a (thio)ether bond in a molecule represented by the general formula (2).

The general formula (2) will be described.

The compound represented by the above general formula (2) is a polythiol compound having at least two thiol groups in a molecule.

In the above general formula (2), $R_1$ represents an organic group. When b is 1, $R_1$ may have at least one thiol group, and when b is 2 or more, $R_1$ may not contain a thiol group. Examples of $R_1$ include a straight chained or branched aliphatic organic group, an alicyclic organic group, a heterocyclic organic group and the like.

b represents a valence of $R_1$.

Furthermore, in the general formula (2), $X_1$s each independently represent a sulfur atom or an oxygen atom. From the viewpoint of high refractive index, $X_1$ is more preferably a sulfur atom.

$R_2$s each independently represent a divalent organic group, and may be bonded to each other to form a group having a cyclic structure.

Such a divalent organic group is more specifically a divalent chained or cyclic aliphatic group, an aromatic group and an aromatic-aliphatic group. Preferable examples thereof include a divalent chained aliphatic group having 1 to 20 carbon atoms, a divalent cyclic aliphatic group having 3 to 20 carbon atoms, a divalent aromatic group having 5 to 20 carbon atoms and a divalent aromatic-aliphatic group having 6 to 20 carbon atoms.

More specifically, preferable examples thereof include a substituted or unsubstituted chained or cyclic aliphatic group having 1 to 20 carbon atoms such as a methylene group, an ethylene group, a 1,2-dichloroethylene group, a trimethylene group, a tetramethylene group, a pentamethylene group, a cyclopentylene group, a hexamethylene group, a cyclohexylene group, a heptamethylene group, an octamethylene group, a nonamethylene group, a decamethylene group, an undecamethylene group, a dodecamethylene group, a tridecamethylene group, a tetradecamethylene group, a pentadecamethylene group and the like;

a substituted or unsubstituted aromatic group having 5 to 20 carbon atoms such as a phenylene group, a chlorophenylene group, a naphthylene group, an indenylene group, an anthracenylene group, a fluorenylene group and the like; and a substituted or unsubstituted aromatic-aliphatic group having 6 to 20 carbon atoms such as a —$C_6H_4$—$CH_2$— group, a —$CH_2$—$C_6H_4$—$CH_2$— group, a —$CH_2$—$C_6H_3$(Cl)—$CH_2$— group, a —$C_{10}H_6$—$CH_2$— group, a —$CH_2$—$C_{10}H_6$—$CH_2$— group, a —$CH_2CH_2$—$C_6H_4$—$CH_2CH_2$— group and the like.

More preferable examples include a substituted or unsubstituted chained or cyclic aliphatic group having 1 to 6 carbon atoms such as a methylene group, an ethylene group, a 1,2-dichloroethylene group, a trimethylene group, a cyclopentylene group, a cyclohexylene group and the like;

a substituted or unsubstituted aromatic group having 5 to 15 carbon atoms such as a phenylene group, a chlorophenylene group, a naphthylene group, an indenylene group, an anthracenylene group, a fluorenylene group and the like; and a substituted or unsubstituted aromatic-aliphatic group having 6 to 15 carbon atoms such as a —$C_6H_4$—$CH_2$— group, a —CH$_2$—C$_6$H$_4$—CH$_2$— group, a —CH$_2$—C$_6$H$_3$(Cl)—CH$_2$— group, a —C$_{10}$H$_6$—CH$_2$— group, a —CH$_2$—C$_{10}$H$_6$—CH$_2$— group, a —CH$_2$CH$_2$—C$_6$H$_4$—CH$_2$CH$_2$— group and the like.

Such a divalent organic group may contain a hetero atom other than a carbon atom and a hydrogen atom in the group. Examples of the hetero atom include an oxygen atom and a sulfur atom. In consideration of the desired effect of the present invention, it is preferable that the divalent organic group contains a sulfur atom in the group.

Examples of the polythiol compound having at least two thiol groups in a molecule include aliphatic polythiols such as methanedithiol, 1,2-ethanedithiol, 1,1-propanedithiol, 1,2-propanedithiol, 1,3-propanedithiol, 2,2-propanedithiol, 1,6-hexanedithiol, 1,2,3-propanetrithiol, 1,1-cyclohexanedithiol, 1,2-cyclohexanedithiol, 2,2-dimethylpropane-1,3-dithiol, 3,4-dimethoxybutane-1,2-dithiol, 2-methylcyclohexane-2,3-dithiol, bicyclo[2,2,1]hepta-exo-cis-2,3-dithiol, 1,1-bis(mercaptomethyl)cyclohexane, thiomalic acid bis(2-mercaptoethyl ester), 2,3-dimercaptosuccinic acid(2-mercaptoethyl ester), 2,3-dimercapto-1-propanol (2-mercaptoacetate), 2,3-dimercapto-1-propanol (3-mercaptoacetate), diethylene glycol bis(2-mercaptoacetate), diethylene glycol bis(3-mercaptopropionate), 1,2-dimercaptopropylmethyl ether, 2,3-dimercaptopropylmethyl ether, 2,2-bis(mercaptomethyl)-1,3-propanedithiol, bis(2-mercaptoethyl)ether, ethylene glycol bis(2-mercaptoacetate), ethylene glycol bis(3-mercaptopropionate), trimethylolpropane tris(2-mercaptoacetate), trimethylolpropane tris(3-mercaptopropionate), pentaerythritol tetrakis(2-mercaptoacetate), pentaerythritol tetrakis(3-mercaptopropionate), 1,2-bis(2-mercaptoethylthio)-3-mercaptopropane) and the like;

aromatic polythiols such as 1,2-dimercaptobenzene, 1,3-dimercaptobenzene, 1,4-dimercaptobenzene, 1,2-bis(mercaptomethyl)benzene, 1,3-bis(mercaptomethyl)benzene, 1,4-bis(mercaptomethyl)benzene, 1,2-bis(mercaptoethyl)benzene, 1,3-bis(mercaptoethyl)benzene, 1,4-bis(mercaptoethyl)benzene, 1,2-bis(mercaptomethyleneoxy)benzene, 1,3-bis(mercaptomethyleneoxy)benzene, 1,4-bis(mercaptomethyleneoxy)benzene, 1,2-bis(mercaptoethyleneoxy)benzene, 1,3-bis(mercaptoethyleneoxy)benzene, 1,4-bis(mercaptoethyleneoxy)benzene, 1,2,3-trimercaptobenzene, 1,2,4-trimercaptobenzene, 1,3,5-trimercaptobenzene, 1,2,3-tris(mercaptomethyl)benzene, 1,2,4-tris(mercaptomethyl)benzene, 1,3,5-tris(mercaptomethyl)benzene, 1,2,3-tris(mercaptoethyl)benzene, 1,2,4-tris(mercaptoethyl)benzene, 1,3,5-tris(mercaptoethyl)benzene, 1,2,3-tris(mercaptomethyleneoxy)benzene, 1,2,4-tris(mercaptomethyleneoxy)benzene, 1,3,5-tris(mercaptomethyleneoxy)benzene, 1,2,3-tris(mercaptoethyleneoxy)benzene, 1,2,4-tris(mercaptoethyleneoxy)benzene, 1,3,5-tris(mercaptoethyleneoxy)benzene, 1,2,3,4-tetramercaptobenzene, 1,2,3,5-tetramercaptobenzene, 1,2,4,5-tetramercaptobenzene, 1,2,3,4-tetrakis(mercaptomethyl)benzene, 1,2,3,5-tetrakis(mercaptomethyl)benzene, 1,2,4,5-tetrakis(mercaptomethyl)benzene, 1,2,3,4-tetrakis(mercaptoethyl)benzene, 1,2,3,5-tetrakis(mercaptoethyl)benzene, 1,2,4,5-tetrakis(mercaptoethyl)benzene, 1,2,3,4-tetrakis(mercaptomethyleneoxy)benzene, 1,2,3,5-tetrakis(mercaptomethyleneoxy)benzene, 1,2,4,5-tetrakis(mercaptomethyleneoxy)benzene, 1,2,3,4-tetrakis(mercaptoethyleneoxy)benzene, 1,2,3,5-tetrakis(mercaptoethyleneoxy)benzene, 1,2,4,5-tetrakis(mercaptoethyleneoxy)benzene, 2,2'-dimercaptobiphenyl, 4,4'-dimercaptobiphenyl, 4,4'-dimercaptobibenzyl, 2,5-toluenedithiol, 3,4-toluenedithiol, 1,4-naphthalenedithiol, 1,5-naphthalenedithiol, 2,6-naphthalenedithiol, 2,7-naphthalenedithiol, 2,4-dimethylbenzene-1,3-dithiol, 4,5-dimethylbenzene-1,3-dithiol, 9,10-anthracenedimethanethiol, 1,3-di(p-methoxyphenyl)propane-2,2-dithiol, 1,3-diphenylpropane-2,2-dithiol, phenylmethane-1,1-dithiol, 2,4-di(p-mercaptophenyl)pentane and the like;

halogen-substituted (chlorine-substituted products, bromine-substituted products or the like) aromatic polythiols such as 2,5-dichlorobenzene-1,3-dithiol, 1,3-di(p-chlorophenyl)propane-2,2-dithiol, 3,4,5-triboromo-1,2-dimercaptobenzene, 2,3,4,6-tetrachlor-1,5-bis(mercaptomethyl)benzene and the like;

polythiols each having a heterocyclic ring such as 2-methylamino-4,6-dithiol-sym-triazine, 2-ethylamino-4,6-dithiol-sym-triazine, 2-amino-4,6-dithiol-sym-triazine, 2-morpholino-4,6-dithiol-sym-triazine, 2-cyclohexylamino-4,6-dithiol-sym-triazine, 2-methoxy-4,6-dithiol-sym-triazine, 2-phenoxy-4,6-dithiol-sym-triazine, 2-thiobenzeneoxy-4,6-dithiol-sym-triazine, 2-thiobutyloxy-4,6-dithiol-sym-triazine and the like;

aromatic polythiols each containing a sulfur atom in addition to the mercapto group such as 1,2-bis(mercaptomethylthio)benzene, 1,3-bis(mercaptomethylthio)benzene, 1,4-bis(mercaptomethylthio)benzene, 1,2-bis(mercaptoethylthio)benzene, 1,3-bis(mercaptoethylthio)benzene, 1,4-bis(mercaptoethylthio)benzene, 1,2,3-tris(mercaptomethylthio)benzene, 1,2,4-tris(mercaptomethylthio)benzene, 1,3,5-tris(mercaptomethylthio)benzene, 1,2,3-tris(mercaptoethylthio)benzene, 1,2,4-tris(mercaptoethylthio)benzene, 1,3,5-tris(mercaptoethylthio)benzene, 1,2,3,4-tetrakis(mercaptomethylthio)benzene, 1,2,3,5-tetrakis(mercaptomethylthio)benzene, 1,2,4,5-tetrakis(mercaptomethylthio)benzene, 1,2,3,4-tetrakis(mercaptoethylthio)benzene, 1,2,3,5-tetrakis(mercaptoethylthio)benzene, 1,2,4,5-tetrakis(mercaptoethylthio)benzene and the like, and alkylated products thereof;

bis(mercaptomethyl)sulfide, bis(mercaptoethyl)sulfide, bis(mercaptopropyl)sulfide, bis(mercaptomethylthio)methane, bis(2-mercaptoethylthio)methane, bis(3-mercaptopropyl)methane, 1,2-bis(mercaptomethylthio)ethane, 1,2-(2-mercaptoethylthio)ethane, 1,2-(3-mercaptopropyl)ethane, 1,3-bis(mercaptomethylthio)propane, 1,3-bis(2-mercaptoethylthio)propane, 1,3-bis(3-mercaptopropylthio)propane, 1,2,3-tris(mercaptomethylthio)propane, 1,2,3-tris(2-mercaptoethylthio)propane, 1,2,3-tris(3-mercaptopropylthio)propane, tetrakis(mercaptomethylthiomethyl)methane, tetrakis(2-mercaptoethylthiomethyl)methane, tetrakis(3-mercaptopropylthiomethyl)methane, bis(2,3-dimercaptopropyl)sulfide, 2,5-dimercapto-1,4-dithiane, bis(mercaptomethyl)disulfide, bis(mercaptoethyl)disulfide, bis(mercaptopropyl)disulfide, 1,5-dimercapto-3-thiapentane and the like, and thioglycolic acid and mercaptopropionic acid esters thereof;

aliphatic polythiols each containing a sulfur atom in addition to the mercapto group such as hydroxymethyl sulfide bis(2-mercaptoacetate), hydroxymethyl sulfide bis(3-mercaptopropionate), hydroxyethyl sulfide bis(2-mercaptoacetate), hydroxyethyl sulfide bis(3-mercaptopropionate), hydroxypropyl sulfide bis(2-mercaptoacetate), hydroxypropyl sulfide bis(3-mercaptopropionate), hydroxymethyl disulfide bis(2-mercaptoacetate), hydroxymethyl disulfide bis(3-mercaptopropionate), hydroxyethyl disulfide bis(2-mercaptoacetate), hydroxyethyl disulfide bis(3-mercaptopropionate), hydroxypropyl disulfide bis(2-mercaptoacetate), hydroxypropyl disulfide bis(3-mercaptopropionate), 2-mercaptoethyl ether bis(2- mercaptoacetate), 2-mercaptoethyl ether bis(3-mercaptopropionate), 1,4-dithiane-2,5-diol bis(2-mercaptoacetate), 1,4-dithiane-2,5-diol bis(3-mercaptopropionate), thiodiglycolic acid bis(2-mercaptoethyl ester), thiodipropionic acid bis(2-mercaptoethyl ester), 4,4-thiodibutylic acid bis(2-mercaptoethyl ester), dithiodiglycolic acid bis(2-mercaptoethyl ester), dithiodipropionic acid bis(2-mercaptoethyl ester), 4,4-dithiodibutylic acid bis(2-mercaptoethyl ester), thiodiglycolic acid bis(2,3-dimercaptopropyl ester), thiodipropionic acid bis(2,3-dimercaptopropyl ester), dithiodiglycolic acid bis(2,3-dimercaptopropyl ester), dithiodipropionic acid (2,3-dimercaptopropyl ester), 2,5-bis(mercaptomethyl)-1,4-dithiane, 4-mercaptomethyl-1,8-dimercapto-3,6-dithiaoctane, 5,7-dimercaptomethyl-1,11-dimercapto-3,6,9-trithiaundecane, 4,7-dimercaptomethyl-1,11-dimercapto-3,6,9-trithiaundecane, 4,8-dimercaptomethyl-1,11-dimercapto-3,6,9-trithiaundecane, 1,1,3,3-tetrakis (mercaptomethylthio)propane, 4,6-bis (mercaptomethylthio)-1,3-dithiane, 2-(2,2-bis (mercaptomethylthio)ethyl)-1,3-dithietane and the like, and mixtures thereof; and heterocyclic compounds each containing a sulfur atom in addition to the mercapto group such as 3,4-thiophenedithiol, 2,5-dimercapto-1,3,4-thiadiazole and the like.

From the viewpoint of high refractive index, preferable examples of the polythiol compound having at least two thiol groups in a molecule include 1,2,3-propanetrithiol, 2,5-dimercapto-1,4-dithiane, 4-mercaptomethyl-1,8-dimercapto-3,6-dithiaoctane, 5,7-dimercaptomethyl-1,11-dimercapto-3,6,9-trithiaundecane, 4,7-dimercaptomethyl-1,11-dimercapto-3,6,9-trithiaundecane, 4,8-dimercaptomethyl-1, 11-dimercapto-3,6,9-trithiaundecane, 1,1,3,3-tetrakis (mercaptomethylthio)propane, 4,6-bis (mercaptomethylthio)-1,3-dithiane, 2-(2,2-bis (mercaptomethylthio)ethyl)-1,3-dithietane and the like. These compounds may be used singly or two or more compounds may be used in combination.

From the viewpoint of high refractive index, it is preferable to use compounds only composed of a carbon atom, a hydrogen atom and a sulfur atom as the polythiol compound, of which a compound represented by the following general formula (3) is further preferably used,

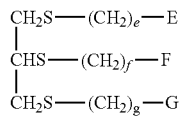

(3)

wherein, in the general formula (3), E to G each represent an SH group or hydrogen; and e, f and g each represent an integer of not less than 0. However, the general formula (3) has at least two mercapto groups.

From the viewpoint of high refractive index, it is further preferable to use 4-mercaptomethyl-1,8-dimercapto-3,6-dithiaoctane.

Incidentally, as described above, from the viewpoint of high refractive index, it is preferable to have a sulfur atom. However, for example, a trithiocarbonate structure or the like is not preferable from the viewpoints of chemical stability, coloring and the like, whereas, as shown in the general formula (3), it is preferable that a trithiocarbonate structure is not contained and a thioether bond is contained. Also, from the viewpoint of Abbe's number, as shown in the general formula (3), it is preferable that an aromatic ring is not contained.

Furthermore, in consideration of the number of metal atoms capable of being bonded per 1 molecule of polythiol, it is preferable to have as many thiol groups as possible in a molecule of polythiol, and for example, it is more preferable to have three or more thiols in a molecule of polythiol.

The reaction of the thiol compound having at least two thiol groups with an Sb or Bi oxide or an Sb or Bi halide will be described hereinafter.

The reaction may be carried out in the absence of a solvent, or may be carried out in the presence of an organic solvent which is inactive to the reaction. The organic solvents are not particularly limited as long as they are inactive to the reaction, and examples thereof include hydrocarbon solvents such as petroleum ether, hexane, benzene, toluene, xylene, mesitylene and the like; ether solvents such as diethyl ether, tetrahydrofuran, diethylene glycol dimethyl ether and the like; ketone solvents such as acetone, methyl ethyl ketone, methyl isobutyl ketone and the like; ester solvents such as ethyl acetate, butyl acetate, amyl acetate and the like; chlorine-containing solvents such as methylene chloride, chloroform, chlorobenzene, dichlorobenzene and the like; and polar aprotic solvents such as N,N-dimethylformamide, N,N-dimethylacetamide, N,N-dimethylimidazolidinone, dimethyl sulfoxide and the like.

The reaction temperature is not particularly limited, but it is usually in the range of from −78 to 200 degrees centigrade, preferably from −78 to 100 degrees centigrade, further preferably from 0 to 100 degrees centigrade, and more preferably from 20 to 100 degrees centigrade.

The reaction time is affected by the reaction temperature, but it is usually from several minutes to 100 hours.

In the reaction, the amounts of the compound represented by the general formula (1) or the Sb or Bi oxide and the polythiol compound having at least two thiol groups in a molecule are not particularly limited, but it is preferable that the amount of the polythiol compound is specified such that the SH group is contained in an excess amount relative to the reaction site of the compound represented by the general formula (1) or the Sb or Bi oxide.

Namely, the amount is specified to be

[valence of a metal(usually 3)×number of metals−
metal substituents(number of Ys)]<[(thiol residues in the polythiol compound)×(number of moles introduced)].

Specifically, in case of $Sb_2O_3$ (number of reaction sections: 6) and 4-mercaptomethyl-1,8-dimercapto-3,6-dithiaoctane (having three thiol groups in a molecule), the molar ratio of the metal oxide to polythiol is specified to be 1/(greater than 2), namely, less than ½. The proportion of 4-mercaptomethyl-1,8-dimercapto-3,6-dithiaoctane is preferably not more than 20 moles, further preferably not less than 3 and not more than 9 moles, and more preferably not less than 4 and not more than 9 moles, based on 1 mole of $Sb_2O_3$.

When the reaction is carried out, it is preferable to use a basic compound as a capturing agent of the generated halogenated hydrogen in order to effectively carry out the reaction. Examples of the basic compound include inorganic bases such as sodium hydroxide, potassium hydroxide, lithium hydroxide, sodium carbonate, potassium carbonate, lithium carbonate, sodium bicarbonate, potassium bicarbonate, lithium bicarbonate, magnesium hydroxide, calcium hydroxide and the like; and organic bases such as pyridine, triethylamine, dimethylaniline, diethylaniline, 1,8-diazabicyclo[5,4,0]-7-undecene and the like.

It is presumed that the product having a thiol group obtained by reacting an Sb or Bi oxide or an Sb or Bi chloride with at least one kind of polythiol compounds selected from compounds having at least two thiol groups in a molecule would contain a compound having a structure represented by the following general formula (O), and having a metal of Sb or Bi and an SH group,

(0)

wherein, M represents Sb or Bi; a represents a valence of M; n represents an integer of not less than 1 and not more than a; Y represents a monovalent inorganic or organic group; and $R_3$ represents a divalent organic group. Incidentally, Y, n and a each represent the same as those in the general formula (1).

The structure of the $-(S-R_3-SH)_n$ portion in the general formula (O) is not particularly limited as long as it is based on the structure of the polythiol compound used in the reaction. Namely, $R_3$ may have the same structure as that of $R_2$ in some cases, but it is not restricted thereto. When the polythiol compound has at least three SH groups in a molecule, the structure may become a cyclic structure (for example, the following formula (4) and the like). When n is not less than 2, $-(S-R_3-SH)$ groups may be bonded to one another to form a group having a cyclic structure, or may be a structure in which $-(S-R_3-SH)$ groups may be bonded to other metal atoms through the polythiol compound residues (for example, the following formula (6) and the like).

For example, it is presumed that when a halide of antimony (for example, $SbCl_3$) or an oxide of antimony (for example, $Sb_2O_3$) is used for reacting with 4-mercaptomethyl-1,8-dimercapto-3,6-dithiaoctane, respective products (formulae (4) to (6)) are obtained as follows, One product of the aforementioned products is obtained, or two or more products are obtained in combination, according to the production conditions in some cases.

Namely, the composition of the present invention may contain one kind of products obtained by reacting an Sb or Bi oxide or an Sb or Bi halide with at least one kind of polythiol compounds selected from compounds having at least two thiol groups in a molecule, or may contain a plurality of products obtained according to the aforementioned reaction. For example, the composition may contain one kind of compounds represented by the above formulae (4) to (6), or may contain at least two compounds. Furthermore, the composition may contain the aforementioned polythiol compound having at least two thiol groups in a molecule.

Similarly to the usual polythiol compound, the aforementioned composition of the present invention forms a polymerizable composition with other reactive polymerizable compounds such as iso(thio)cyanate, epoxy, episulfide, thiethane, acryl and the like.

That is, the polymerizable composition containing the composition of the present invention may contain at least one kind of compounds selected from the group consisting of an active hydrogen compound and other reactive polymerizable compounds, for example, an iso(thio)cyanate compound, an epoxy compound, an epithio compound, a thietane compound, a (meth)acrylate ester compound and a vinyl compound, as other components. In this way, it is possible to obtain a transparent member with an enhanced refractive index.

(4)

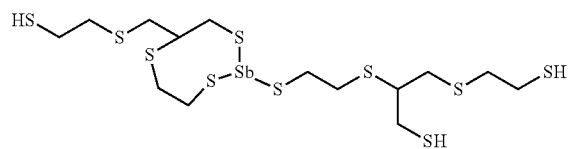

(5)

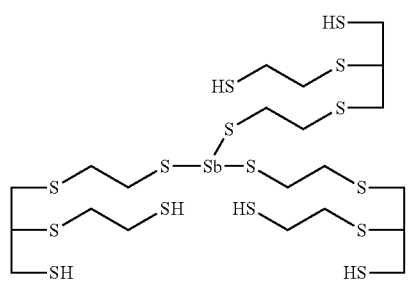

(6)

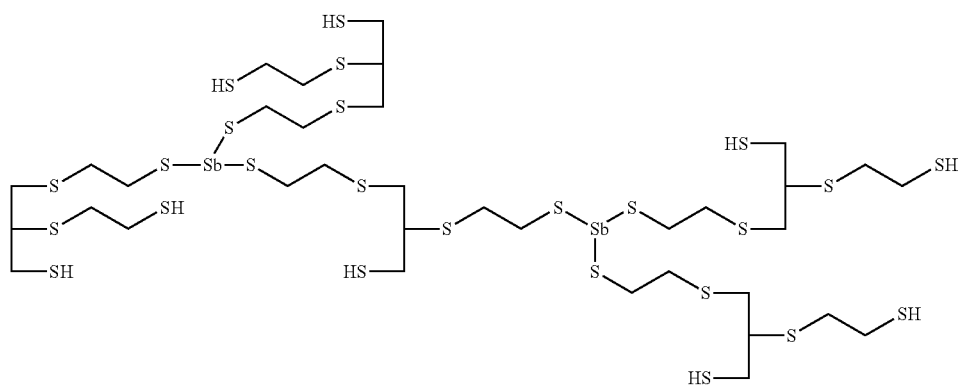

Active Hydrogen Compound

The active hydrogen compound used in the present invention is a compound having active hydrogen (for example, a thiol group or a hydroxyl group). The active hydrogen compound is specifically selected from a polyol compound, a thiol compound and a hydroxythiol compound. This active hydrogen compound may be the same compound as the aforementioned polythiol compound having at least two thiol groups in a molecule. However, it is preferable that the active hydrogen compound is different from the aforementioned product obtained by reacting an Sb or Bi oxide or an Sb or Bi halide with at least one kind of polythiol compounds selected from compounds having at least two thiol groups in a molecule.

Examples of the polyol compound include aliphatic polyols such as ethylene glycol, diethylene glycol, propylene glycol, dipropylene glycol, butylene glycol, neopentyl glycol, glycerine, trimethylolethane, trimethylolpropane, butanetriol, 1,2-methyl glycoside, pentaerythritol, dipentaerythritol, tripentaerythritol, sorbitol, erythritol, threitol, ribitol, arabinitol, xylitol, allitol, mannitol, dulcitol, iditol, glycol, inositol, hexanetriol, triglycerose, diglyperol, triethylene glycol, polyethylene glycol, tris(2-hydroxyethyl)isocyanurate, cyclobutanediol, cyclopentanediol, cyclohexanediol, cycloheptanediol, cyclooctanediol, cyclohexane dimethanol, hydroxypropyl cyclohexanol, tricyclo[5.2.1.0$^{2,6}$]decane-dimethanol, bicyclo[4,3,0]-nonanediol, dicyclohexanediol, tricyclo[5,3,1,1]dodecanediol, bicyclo[4,3,0]nonanedimethanol, tricyclo[5,3,1,1]dodecane-diethanol, hydroxypropyltricyclo[5,3,1,1]dodecanol, spiro[3,4]octanediol, butylcyclohexanediol, 1,1'-bicyclohexylidenediol, cyclohexanetriol, maltitol, lactose and the like;

aromatic polyols such as dihydroxynaphthalene, tirhydroxynaphthalene, tetrahydroxynaphthalene, dihydroxybenzene, benzenetriol, biphenyltetraol, pyrogallol, (hydroxynaphthyl)pyrogallol, trihydroxyphenanthrene, bisphenol A, bisphenol F, xylilene glycol, di(2-hydroxyethoxy)benzene, bisphenol A-bis-(2-hydroxyethyl ether), tetrabromobisphenol A, tetrabromobisphenol A-bis-(2-hydroxyethyl ether) and the like;

halogenated polyols such as dibromoneopentyl glycol and the like; and high molecular polyols such as an epoxy resin and the like.

Examples of other polythiol compounds include condensation products of aforementioned polyols with organic acids such as oxalic acid, glutamic acid, adipic acid, acetic acid, propionic acid, cyclohexanecarboxylic acid, β-oxocyclohexanepropionic acid, dimer acid, phthalic acid, isophthalic acid, salicylic acid, 3-bromopropionic acid, 2-bromoglycol, dicarboxycyclohexane, pyromellitic acid, butanetetracarboxylic acid, bromophthalic acid and the like;

addition products between aforementioned polyols and an alkylene oxide such as ethylene oxide, propylene oxide or the like;

addition products between alkylenepolyamine and alkylene oxide such as ethylene oxide, propylene oxide or the like;

bis-[4-(hydroxyethoxy)phenyl]sulfide, bis-[4-(2-hydroxypropoxy)phenyl]sulfide, bis-[4-(2,3-dihydroxypropoxy)phenyl]sulfide, bis-[4-(4-hydroxycyclohexyloxy)phenyl]sulfide, bis-[2-methyl-4-(hydroxyethoxy)-6-butylphenyl] sulfide and compounds obtained by adding not more than 3 molecules on the average of ethylene oxide and/or propylene oxide per hydroxyl group to these compounds; and polyols each containing a sulfur atom such as di-(2-hydroxyethyl)sulfide, 1,2-bis-(2-hydroxyethylmercapto)ethane, bis(2-hydroxyethyl)disulfide, 1,4-dithiane-2,5-diol, bis(2,3-dihydroxypropyl)sulfide, tetrakis(4-hydroxy-2-thiabutyl)methane, bis(4-hydroxyphenyl)sulfone (trade name: Bisphenol S), tetrabromobisphenol S, tetramethylbisphenol S, 4,4'-thiobis(6-tert-butyl-3-methylphenol), 1,3-bis(2-hydroxyethylthioethyl)-cyclohexane and the like.

Examples of the monovalent thiol compound include aliphatic mercaptan compounds such as methyl mercaptan, ethyl mercaptan, propyl mercaptan, butyl mercaptan, octyl mercaptan, dodecyl mercaptan, tert-dodecyl mercaptan, hexadecyl mercaptan, octadecyl mercaptan, cyclohexyl mercaptan, benzyl mercaptan, ethylphenyl mercaptan, 2-mercaptomethyl-1,3-dithiolane, 2-mercaptomethyl-1,4-dithiane, 1-mercapto-2,3-epithiopropane, 1-mercaptomethylthio-2,3-epithiopropane, 1-mercaptoethylthio-2,3-epithiopropane, 3-mercaptothietane, 2-mercaptothietane, 3-mercaptomethylthiothietane, 2-mercaptomethylthiothietane, 3-mercaptoethylthiothietane, 2-mercaptoethylthiothietane and the like;

aromatic mercaptan compounds such as thiophenol, mercaptotoluene and the like; and compounds each having a hydroxyl group in addition to the mercapto group such as 2-mercaptoethanol, 3-mercapto-1,2-propanediol and the like.

As the polythiol compound, there can be cited the aforementioned polythiol compounds having at least two thiol groups in a molecule.

Examples of the hydroxythiol compound include 2-mercaptoethanol, 3-mercapto-1,2-propanediol, glycerine di(mercaptoacetate), 1-hydroxy-4-mercaptocyclohexane, 2,4-dimercaptophenol, 2-mercaptohydroquinone, 4-mercaptophenol, 3,4-dimercapto-2-propanol, 1,3-dimercapto-2-propanol, 2,3-dimercapto-1-propanol, 1,2-dimercapto-1,3-butanediol, pentaerythritol tris(3-mercaptopropionate), pentaerythritol mono(3-mercaptopropionate), pentaerythritol bis(3-mercaptopropionate), pentaerythritol tris(thioglycolate), pentaerythritol pentakis(3-mercaptopropionate), hydroxymethyl-tris(mercaptoethylthiomethyl) methane, 1-hydroxyethylthio-3-mercaptoethylthiobenzene, 4-hydroxy-4'-mercaptodiphenylsulfone, 2-(2-mercaptoethylthio)ethanol, dihydroxyethyl sulfide mono(3-mercaptopropionate), dimercaptoethane mono(salicylate), hydroxyethylthiomethyl-tris(mercaptoethylthio)methane and the like.

Furthermore, halogen-substituted products such as chlorine-substituted products and bromine-substituted products of these active hydrogen compounds may also be used. These products may be used singly or two or more kinds may be used in combination.

When a thiol compound is used as an active hydrogen compound, in consideration of optical physical properties of the obtained resin, particularly Abbe's number, it is preferable to select an aliphatic thiol compound rather than an aromatic thiol compound. Furthermore, in consideration of optical physical properties, particularly the demand of refractive index, it is more preferable to select a compound having a sulfur group in addition to the thiol group such as a sulfide bond and/or a disulfide bond. In consideration of heat resistance of the obtained resin, it is particularly preferable to select at least one kind of thiol compounds having a polymerizable group such as an epithio group or a thietanyl group, at least one kind of compounds having at least three thiol groups in order to increase three-dimensional cross-linking property.

From the above viewpoint, preferable examples of the thiol compound include 1-mercapto-2,3-epithiopropane, 1-mercaptomethylthio-2,3-epithiopropane, 1-mercaptoethylthio-2,3-epithiopropane, 3-mercaptothietane, 2-mercaptothietane, 3-mercaptomethylthiothietane, 2-mercaptomethylthiothietane, 3-mercaptoethylthiothietane, 2-mercaptoethylthiothietane, 2,5-bis(mercaptomethyl)-1,4-dithiane, 4-mercaptomethyl-1,8-dimercapto-3,6-dithiaoctane, 4,8-dimercaptomethyl-1,11-dimercapto-3,6,9-trithiaundecane, 4,7-dimercaptomethyl-1,11-dimercapto-3,6,9-trithiaundecane, 5,7-dimercaptomethyl-1,11-dimercapto-3,6,9-trithiaundecane, 1,1,1,1-tetrakis(mercaptomethyl)methane, 1,1,3,3-tetrakis(mercaptomethylthio)propane, 1,1,2,2-tetrakis(mercaptomethylthio)ethane, 4,6-bis(mercaptomethylthio)-1,3-dithiane, 2-(2,2-bis(mercaptomethylthio)ethyl)-1,3-dithietane and 1,2-ethanedithiol.

Further preferable examples thereof include 3-mercaptothietane, 4-mercaptomethyl-1,8-dimercapto-3,6-dithiaoctane, 2,5-bis(mercaptomethyl)-1,4-dithiane, 4,8-dimercaptomethyl-1,11-dimercapto-3,6,9-trithiaundecane, 4,7-dimercaptomethyl-1,11-dimercapto-3,6,9-trithiaundecane, 5,7-dimercaptomethyl-1,11-dimercapto-3,6,9-trithiaundecane, 1,1,1,1-tetrakis(mercaptomethyl)methane, 1,1,3,3-tetrakis(mercaptomethylthio)propane, 1,1,2,2-tetrakis(mercaptomethylthio)ethane, 4,6-bis(mercaptomethylthio)-1,3-dithiane, 2-(2,2-bis(mercaptomethylthio)ethyl)-1,3-dithietane and 1,2-ethanedithiol. Furthermore, when a divalent thiol compound is selected, it is preferable that a thiol compound having a polymerizable group and/or a tri- or higher valent thiol compound are mixed together prior to use.

The thiol compound is further specifically at least one kind of compounds selected from the group consisting of 3-mercaptothietane, 1,2-ethanedithiol, 4-mercaptomethyl-1,8-dimercapto-3,6-dithiaoctane, 4,8-dimercaptomethyl-1,11-dimercapto-3,6,9-trithiaundecane and 2,5-bis(mercaptomethyl)-1,4-dithiane.

Isocyanate Compound

Examples of the isocyanate compound include compounds each containing at least one kind of isocyanate groups (NCO groups) in a molecule.

The isocyanate compound is not particularly limited, but preferably used is a polyisocyanate compound having a plurality of isocyanate groups, and further preferably used is a diisocyanate compound.

Concrete examples thereof include aliphatic polyisocyanate compounds such as 1,6-hexamethylene diisocyanate, 2,2-dimethylpentane diisocyanate, 2,2,4-trimethylhexane diisocyanate, butene-1,4-diisocyanate, 1,3-butadiene-1,4-diisocyanate, 2,4,4-trimethylhexamethylene diisocyanate, 1,6,11-undecane triisocyanate, 1,3,6-hexamethylene triisocyanate, 1,8-diisocyanato-4-isocyanatomethyloctane, bis(isocyanatoethyl)carbonate, bis(isocyanatoethyl)ether, lysine diisocyanatomethyl ester, lysine triisocyanate, xylylene diisocyanate, bis(isocyanatoethyl)benzene, bis(isocyanatopropyl)benzene, α,α,α',α'-tetramethylxylylene diisocyanate, bis(isocyanatobutyl)benzene, bis(isocyanatomethyl)naphthalene, bis(isocyanatomethylphenyl)ether, bis(isocyanatoethyl)phthalate, 2,6-di(isocyanatomethyl)furan, bis(isocyanatomethyl)bicyclo-[2,2,1]-heptane and the like;

alicyclic polyisocyanate compounds such as isophorone diisocyanate, bis(isocyanatomethyl)cyclohexane, cyclohexane diisocyanate, methylcyclohexane diisocyanate, 4,4'-methylene bis(cyclohexyl isocyanate), 4,4'-methylene bis(2-methylcyclohexyl isocyanate), dicyclohexylmethane diisocyanate, 2,5-bis(isocyanatomethyl)bicyclo-[2,2,1]-heptane, 2,6-bis(isocyanatomethyl)bicyclo-[2,2,1]-heptane, 3,8-bis(isocyanatomethyl)tricyclodecane, 3,9-bis(isocyanatomethyl)tricyclodecane, 4,8-bis(isocyanatomethyl)tricyclodecane, 4,9-bis(isocyanatomethyl)tricyclodecane, isophorone diisocyanate and the like;

aromatic polyisocyanate compounds such as 1,2-diisocyanatobenzene, 1,3-diisocyanatobenzene, 1,4-diisocyanatobenzene, m-xylylene diisocyanate, 2,4-diisocyanatotoluene, toluene diisocyanate, ethylphenylene diisocyanate, isopropylphenylene diisocyanate, dimethylphenylene diisocyanate, diethylphenylene diisocyanate, diisopropylphenylene diisocyanate, trimethylbenzene triisocyanate, benzene triisocyanate, biphenyl diisocyanate, tolidine diisocyanate, 4,4'-methylene bis(phenyl isocyanate), 4,4'-methylene bis(2-methylphenyl isocyanate), bibenzyl-4,4'-diisocyanate, bis(isocyanatophenyl)ethylene and the like;

sulfur-containing aliphatic polyisocyanate compounds such as bis(isocyanatomethyl)sulfide, bis(isocyanatoethyl)sulfide, bis(isocyanatopropyl)sulfide, bis(isocyanatohexyl)sulfide, bis(isocyanatomethyl)sulfone, bis(isocyanatomethyl)disulfide, bis(isocyanatoethyl)disulfide, bis(isocyanatopropyl)disulfide, bis(isocyanatomethylthio)methane, bis(isocyanatoethylthio)methane, bis(isocyanatoethylthio)ethane, bis(isocyanatomethylthio)ethane, 1,5-diisocyanato-2-isocyanatomethyl-3-thiapentane, 1,2,3-tris(isocyanatomethylthio)propane, 1,2,3-tris(isocyanatoethylthio)propane, 3,5-dithia-1,2,6,7-heptane tetraisocyanate, 2,6-diisocyanatomethyl-3,5-dithia-1,7-heptane diisocyanate, 2,5-diisocyanatemethylthiophene, 4-isocyanatoethylthio-2,6-dithia-1,8-octane diisocyanate and the like;

aromatic sulfide type polyisocyanate compounds such as 2-isocyanatophenyl-4-isocyanatophenyl sulfide, bis(4-isocyanatophenyl)sulfide, bis(4-isocyanatomethylphenyl)sulfide and the like;

aromatic disulfide type polyisocyanate compounds such as bis(4-isocyanatophenyl)disulfide, bis(2-methyl-5-isocyanatophenyl)disulfide, bis(3-methyl-5-isocyanatophenyl)disulfide, bis(3-methyl-6-isocyanatophenyl)disulfide, bis(4-methyl-5-isocyanatophenyl)disulfide, bis(3-methoxy-4-isocyanatophenyl)disulfide, bis(4-methoxy-3-isocyanatophenyl)disulfide and the like;

sulfur-containing alicyclic polyisocyanate compounds such as 2,5-diisocyanatotetrahydrothiophene, 2,5-diisocyanatomethyltetrahydrothiophene, 3,4-diisocyanatomethyltetrahydrothiophene, 2,5-diisocyanato-1,4-dithiane, 2,5-diisocyanatomethyl-1,4-dithiane, 4,5-diisocyanato-1,3-dithiolane, 4,5-bis(isocyanatomethyl)-1,3-dithiolane, 4,5-diisocyanatomethyl-2-methyl-1,3-dithiolane and the like; and compounds each having an isocyanate group and an isothiocyanate group such as 1-isocyanato-6-isothiocyanatohexane, 1-isocyanato-4-isothiocyanatocyclohexane, 1-isocyanato-4-isothiocyanatobenzene, 4-methyl-3-isocyanato-1-isothiocyanatobenzene, 2-isocyanato-4,6-diisothiocyanato-1,3,5-triazine, 4-isocyanatophenyl-4-isothiocyanatophenylsulfide, 2-isocyanatoethyl-2-isothiocyanatoethyl disulfide and the like.

In addition, halogen-substituted products of these compounds such as chlorine-substituted products, bromine-substituted products or the like, alkyl-substituted products, alkoxy-substituted products, nitro-substituted products, prepolymer type modified products modified with polyhydric alcohols, carbodiimide modified products, urea modified products, biuret modified products, dimerization or trimerization reaction products or the like can also be used.

Preferable examples thereof include 1,6-hexamethylene diisocyanate, bis(isocyanatomethyl)cyclohexane, m-xylylene diisocyanate, dicyclohexylmethane diisocyanate, 2,5-diisocyanatomethyl-1,4-dithiane, 4,5-diisocyanato-1,3-dithiolane, toluene diisocyanate, bis(isocyanatomethyl)bicyclo-[2,2,1]-heptane, isophorone diisocyanate and the like.

Further preferable examples include m-xylylene diisocyanate, bis(isocyanatomethyl)bicyclo[2.2.1]heptane and the like.

Specifically, as an active hydrogen compound to be added to the polyisocyanate compound, thiol compounds, preferably 4-mercaptomethyl-1,8-dimercapto-3,6-dithiaoctane and the like, can be used in combination thereof.

Polyisothiocyanate Compound

The polyisothiocyanate compound is a compound containing at least one of isothiocyanate groups (NCS groups) in a molecule, and is not particularly limited. However, preferably used is a polyisothiocyanate compound having a plurality of isothiocyanate groups, and further preferably used is a dithioisocyanate compound. A compound in which the isocyanate group (NCO group) of the above polyisocyanate compound is replaced with the isothiocyanate group (NCS group) is cited.

Preferable examples thereof include butane-1,4-diisothiocyanate, 1,6-hexamethylene diisothiocyanate, bis(isothiocyanatomethyl)cyclohexane, m-xylylene diisothiocyanate, dicyclohexylmethane diisothiocyanate, 2,5-diisothiocyanatomethyl-1,4-dithiane, 4,5-diisothiocyanato-1,3-dithiolane, toluene diisothiocyanate, bis(isothiocyanatomethyl)bicyclo-[2,2,1]-heptane, and isophorone dithioisocyanate.

A further preferable example includes butane-1,4-diisothiocyanate.

Specifically, as an active hydrogen compound to be added to the aforementioned polyisothiocyanate compound, thiol compounds, preferably 4-mercaptomethyl-1,8-dimercapto-3,6-dithiaoctane, and the like, can be used in combination thereof.

In addition, examples include aliphatic polyisothiocyanate compounds such as 1,2-diisothiocyanatoethane, 1,6-diisothiocyanatohexane and the like;

alicyclic polyisothiocyanate compounds such as cyclohexane diisothiocyanate and the like; and aromatic polyisothiocyanate compounds such as 1,2-diisothiocyanatobenzene, 1,3-diisothiocyanatobenzene, 1,4-diisothiocyanatobenzene, 2,4-diisothiocyanatotoluene, 2,5-diisothiocyanato-m-xylene, 4,4'-diisothiocyanatobiphenyl, 4,4'-methylene bis(phenyl isothiocyanate), 4,4'-methylene bis(2-methylphenyl isothiocyanate), 4,4'-methylene bis(3-methylphenyl isothiocyanate), 4,4'-isopropylidene bis(phenyl isothiocyanate), 4,4'-diisothiocyanatobenzophenone, 4,4'-diisothiocyanato-3,3'-dimethylbenzophenone, bis(4-isothiocyanatophenyl)ether and the like.

Further examples thereof include carbonyl polyisothiocyanate compounds such as 1,3-benzenedicarbonyl diisothiocyanate, 1,4-benzenedicarbonyl diisothiocyanate, (2,2-pyridine)-4,4-dicarbonyl diisothiocyanate and the like;

sulfur-containing aliphatic polyisothiocyanate compounds such as thiobis(3-isothiocyanatopropane), thiobis(2-isothiocyanatoethane), dithiobis(2-isothiocyanatoethane) and the like;

sulfur-containing aromatic polyisothiocyanate compounds such as 1-isothiocyanato-4-[(2-isothiocyanato)sulfonyl]benzene, thiobis(4-isothiocyanatobenzene), sulfonyl bis(4-isothiocyanatobenzene), dithiobis(4-isothiocyanatobenzene) and the like; and sulfur-containing alicyclic polyisothiocyanate compounds such as 2,5-diisothiocyanatothiophene, 2,5-diisothiocyanato-1,4-dithiane and the like.

Epoxy Compound

The epoxy compound and the epithio compound each contain one or more epoxy groups and one or more epithio groups in a molecule. Furthermore, they are each preferably a compound containing two or more epoxy groups and/or epithio groups in total.

Concrete examples of the epoxy compound include a phenol type epoxy compound obtained by the condensation reaction of a polyhydric phenol compound such as bisphenol A, bisphenol F and the like with an epihalohydrin compound (for example, bisphenol A glycidyl ether, bisphenol F glycidyl ether);

an alcohol type epoxy compound obtained by condensation of a polyhydric alcohol compound such as hydrogenated bisphenol A, hydrogenated bisphenol F, cyclohexane dimethanol and the like with an epihalohydrin compound (for example, hydrogenated bisphenol A glycidyl ether, hydrogenated bisphenol F glycidyl ether), and other alcohol type epoxy compounds such as ethylene glycol diglycidyl ether, neopentyl glycol diglycidyl ether, 1,4-cyclohexane dimethanol diglycidyl ether, trimethylolpropane triglycidyl ether and the like;

a glycidyl ester type epoxy compound such as 3,4-epoxycyclohexylmethyl-3',4'-epoxycyclohexane carboxylate, 1,2-hexahydrophthalic acid diglycidyl ester and the like; and an amine type epoxy compound obtained by condensation of primary and secondary amine compounds with an epihalohydrin compound (for example, triglycidyl ether isocyanurate). In addition thereto, an aliphatic polyvalent epoxy compound such as vinylcyclohexene diepoxide including 4-vinyl-1-cyclohexane diepoxide and the like can be cited.

Concrete examples of the epoxy compound having a sulfide group and the epoxy compound having an ether group include chained aliphatic 2,3-epoxypropylthio compounds such as bis(2,3-epoxypropyl)sulfide, bis(2,3-epoxypropyl)disulfide, bis(2,3-epoxypropylthio)methane, 1,2-bis(2,3-epoxypropylthio)ethane, 1,2-bis(2,3-epoxypropylthio)propane, 1,3-bis(2,3-epoxypropylthio)propane, 1,3-bis(2,3-epoxypropylthio)-2-methylpropane, 1,4-bis(2,3-epoxypropylthio)butane, 1,4-bis(2,3-epoxypropylthio)-2-methylbutane, 1,3-bis(2,3-epoxypropylthio)butane, 1,5-bis(2,3-epoxypropylthio)pentane, 1,5-bis(2,3-epoxypropylthio)-2-methylpentane, 1,5-bis(2,3-epoxypropylthio)-3-thiapentane, 1,6-bis(2,3-epoxypropylthio)hexane, 1,6-bis(2,3-epoxypropylthio)-2-methylhexane, 3,8-bis(2,3-epoxypropylthio)-3,6-dithiaoctane, 1,2,3-tris(2,3-epoxypropylthio)propane, 2,2-bis(2,3-epoxypropylthio)-1,3-bis(2,3-epoxypropylthiomethyl) propane, 2,2-bis(2,3-epoxypropylthiomethyl)-1-(2,3-epoxypropylthio)butane, 1,5-bis(2,3-epoxypropylthio)-2-(2,3-epoxypropylthiomethyl)-3-thiapentane, 1,5-bis(2,3-epoxypropylthio)-2,4-bis(2,3-epoxypropylthiomethyl-3-thiapentane, 1-(2,3-epoxypropylthio)-2,2-bis(2,3-epoxypropylthiomethyl)-4-thiahexane, 1,5,6-tris(2,3-epoxypropylthio)-4-(2,3-epoxypropylthiomethyl)-3-thiahexane, 1,8-bis(2,3-epoxypropylthio)-4-(2,3-epoxypropylthiomethyl)-3,6-dithiaoctane, 1,8-bis(2,3-epoxypropylthio)-4,5-bis(2,3-epoxypropylthiomethyl)-3,6-dithiaoctane, 1,8-bis(2,3-epoxypropylthio)-4,4-bis(2,3-epoxypropylthiomethyl)-3,6-dithiaoctane, 1,8-bis(2,3-epoxypropylthio)-2,5-bis(2,3-epoxypropylthiomethyl)-3,6-dithiaoctane, 1,8-bis(2,3-epoxypropylthio)-2,4,5-tris(2,3-epoxypropylthiomethyl)-3,6-dithiaoctane, 1,1,1-tris[[2-(2,3-epoxypropylthio)ethyl]thiomethyl]-2-(2,3-epoxypropylthio)ethane, 1,1,2,2-tetrakis[[2-(2,3-epoxypropylthio)ethyl]thiomethyl]ethane, 1,11-bis(2,3-epoxypropylthio)-4,8-bis(2,3-epoxypropylthiomethyl)-3,6,9-trithiaundecane, 1,11-bis(2,3-epoxypropylthio)-4,7-bis(2,3-epoxypropylthiomethyl)-3,6,9-trithiaundecane, 1,11-bis(2,3-epoxypropylthio)-5,7-bis(2,3-epoxypropylthiomethyl)-3,6,9-trithiaundecane, 1,5-bis(glycidylthio)-3-thiapentane and the like;

cyclic aliphatic 2,3-epoxypropylthio compounds such as 1,3-bis(2,3-epoxypropylthio)cyclohexane, 1,4-bis(2,3-epoxypropylthio)cyclohexane, 1,3-bis(2,3-epoxypropylthiomethyl)cyclohexane, 1,4-bis(2,3-epoxypropylthiomethyl)cyclohexane, 2,5-bis(2,3-epoxypropylthiomethyl)-1,4-dithiane, 2,5-bis[[2-(2,3-epoxypropylthio)ethyl]thiomethyl]-1,4-dithiane, 2,5-bis(2,3-epoxypropylthiomethyl)-2,5-dimethyl-1,4-dithiane, 3-(2,3-epoxypropylthio)thietane and the like;

aromatic 2,3-epoxypropylthio compounds such as 1,2-bis(2,3-epoxypropylthio)benzene, 1,3-bis(2,3-epoxypropylthio)benzene, 1,4-bis(2,3-epoxypropylthio)benzene, 1,2-bis(2,3-epoxypropylthiomethyl)benzene, 1,3-bis(2,3-epoxypropylthiomethyl)benzene, 1,4-bis(2,3-epoxypropylthiomethyl)benzene, bis[4-(2,3-epoxypropylthio)phenyl]methane, 2,2-bis[4-(2,3-epoxypropylthio)phenyl]propane, bis[4-(2,3-epoxypropylthio)phenyl]sulfide, bis[4-(2,3-epoxypropylthio)phenyl]sulfone, 4,4'-bis(2,3-epoxypropylthio)biphenyl and the like;

monofunctional epoxy compounds such as ethylene oxide, propylene oxide, glycidol, epichlorohydrin and the like;

chained aliphatic 2,3-epoxypropyloxy compounds such as bis(2,3-epoxypropyl)ether, bis(2,3-epoxypropyloxy)methane, 1,2-bis(2,3-epoxypropyloxy)ethane, 1,2-bis(2,3-epoxypropyloxy)propane, 1,3-bis(2,3-epoxypropyloxy)propane, 1,3-bis(2,3-epoxypropyloxy)-2-methylpropane, 1,4-bis(2,3-epoxypropyloxy)butane, 1,4-bis(2,3-epoxypropyloxy)-2-methylbutane, 1,3-bis(2,3-epoxypropyloxy)butane, 1,5-bis(2,3-epoxypropyloxy)pentane, 1,5-bis(2,3-epoxypropyloxy)-2-methylpentane, 1,5-bis(2,3-epoxypropyloxy)-3-thiapentane, 1,6-bis(2,3-epoxypropyloxy)hexane, 1,6-bis(2,3-epoxypropyloxy)-2-methylhexane, 3,8-bis(2,3-epoxypropyloxy)-3,6-dithiaoctane, 1,2,3-tris(2,3-epoxypropyloxy)propane, 2,2-bis(2,3-epoxypropyloxy)-1,3-bis(2,3-epoxypropyloxymethyl)propane, 2,2-bis(2,3-epoxypropyloxymethyl)-1-(2,3-epoxypropyloxy)butane, 1,5-bis(2,3-epoxypropyloxy)-2-(2,3-epoxypropyloxymethyl)-3-thiapentane, 1,5-bis(2,3-epoxypropyloxy)-2,4-bis(2,3-epoxypropyloxymethyl)-3-thiapentane, 1-(2,3-epoxypropyloxy)-2,2-bis(2,3-epoxypropyloxymethyl)-4-thiahexane, 1,5,6-tris(2,3-epoxypropyloxy)-4-(2,3-epoxypropyloxymethyl)-3-thiahexane, 1,8-bis(2,3-epoxypropyloxy)-4-(2,3-epoxypropyloxymethyl)-3,6-dithiaoctane, 1,8-bis(2,3-epoxypropyloxy)-4,5-bis(2,3-epoxypropyloxymethyl)-3,6-dithiaoctane, 1,8-bis(2,3-epoxypropyloxy)-4,4-bis(2,3-epoxypropyloxymethyl)-3,6-dithiaoctane, 1,8-bis(2,3-epoxypropyloxy)-2,5-bis(2,3-epoxypropyloxymethyl)-3,6-dithiaoctane, 1,8-bis(2,3-epoxypropyloxy)-2,4,5-tris(2,3-epoxypropyloxymethyl)-3,6-dithiaoctane, 1,1,1-tris[[2-(2,3-epoxypropyloxy)ethyl]thiomethyl]-2-(2,3-epoxypropyloxy)ethane, 1,1,2,2-tetrakis[[2-(2,3-epoxypropyloxy)ethyl]thiomethyl]ethane, 1,11-bis(2,3-epoxypropyloxy)-4,8-bis(2,3-epoxypropyloxymethyl)-3,6,9-trithiaundecane, 1,11-bis(2,3-epoxypropyloxy)-4,7-bis(2,3-epoxypropyloxymethyl)-3,6,9-trithiaundecane, 1,11-bis(2,3-epoxypropyloxy)-5,7-bis(2,3-epoxypropyloxymethyl)-3,6,9-trithiaundecane and the like;

cyclic aliphatic 2,3-epoxypropyloxy compounds such as 1,3-bis(2,3-epoxypropyloxy)cyclohexane, 1,4-bis(2,3-epoxypropyloxy)cyclohexane, 1,3-bis(2,3-epoxypropyloxymethyl)cyclohexane, 1,4-bis(2,3-epoxypropyloxymethyl)cyclohexane, 2,5-bis(2,3-epoxypropyloxymethyl)-1,4-dithiane, 2,5-bis[[2-(2,3-epoxypropyloxy)ethyl]thiomethyl]-1,4-dithiane, 2,5-bis(2,3-epoxypropyloxymethyl)-2,5-dimethyl-1,4-dithiane and the like; and aromatic 2,3-epoxypropyloxy compounds such as 1,2-bis(2,3-epoxypropyloxy)benzene, 1,3-bis(2,3-epoxypropyloxy)benzene, 1,4-bis(2,3-epoxypropyloxy)benzene, 1,2-bis(2,3-epoxypropyloxymethyl)benzene, 1,3-bis(2,3-epoxypropyloxymethyl)benzene, 1,4-bis(2,3-epoxypropyloxymethyl)benzene, bis[4-(2,3-epoxypropyloxy)phenyl]methane, 2,2-bis[4-(2,3-epoxypropyloxy)phenyl]propane, bis[4-(2,3-epoxypropyloxy)phenyl]sulfide, bis[4-(2,3-epoxypropyloxy)phenyl]sulfone, 4,4'-bis(2,3-epoxypropyloxy)biphenyl and the like, but are not restricted to these exemplified compounds alone.

Of these exemplified epoxy compounds, preferable examples include bis(2,3-epoxypropyl)disulfide; 4-vinyl-1-cyclohexane diepoxide; a phenol type epoxy compound such as bisphenol A glycidyl ether, bisphenol F glycidyl ether and the like;

an alcohol type epoxy compound such as hydrogenated bisphenol A glycidyl ether, hydrogenated bisphenol F glycidyl ether, ethylene glycol diglycidyl ether, neopentyl glycol diglycidyl ether, 1,4-cyclohexane dimethanol diglycidyl ether, trimethylolpropane triglycidyl ether and the like;

a glycidyl ester type epoxy compound such as 3,4-epoxycyclohexylmethyl-3',4'-epoxycyclohexane carboxylate, 1,2-hexahydrophthalic acid diglycidyl ester and the like; and an amine type epoxy compound such as triglycidyl ether isocyanurate and the like. In addition thereto, an aliphatic polyvalent epoxy compound such as vinylcyclohexene diepoxide and the like can be cited.

More preferable examples of the epoxy compound include bis(2,3-epoxypropyl)disulfide, 1,4-cyclohexane dimethanol diglycidyl ether, bisphenol A glycidyl ether, bisphenol F glycidyl ether, ethylene glycol diglycidyl ether, neopentyl glycol diglycidyl ether, trimethylolpropane triglycidyl ether and triglycidyl ether isocyanurate. Further preferable examples thereof include 1,4-cyclohexane dimethanol diglycidyl ether and bisphenol F glycidyl ether.

Eipithio Compound

Concrete examples of the epithio compound include epithioethylthio compounds such as bis(1,2-epithioethyl)sulfide, bis(1,2-epithioethyl)disulfide, bis(epithioethylthio)methane, bis(epithioethylthio)benzene, bis[4-(epithioethylthio)phenyl]sulfide, bis[4-(epithioethylthio)phenyl]methane and the like;

chained aliphatic 2,3-epithiopropylthio compounds such as bis(2,3-epithiopropyl)sulfide, bis(2,3-epithiopropyl)disulfide, bis(2,3-epithiopropylthio)methane, 1,2-bis(2,3-epithiopropylthio)ethane, 1,2-bis(2,3-epithiopropylthio)propane, 1,3-bis(2,3-epithiopropylthio)propane, 1,3-bis(2,3-epithiopropylthio)-2-methylpropane, 1,4-bis(2,3-epithiopropylthio)butane, 1,4-bis(2,3-epithiopropylthio)-2-methylbutane, 1,3-bis(2,3-epithiopropylthio)butane, 1,5-bis(2,3-epithiopropylthio)pentane, 1,5-bis(2,3-epithiopropylthio)-2-methylpentane, 1,5-bis(2,3-epithiopropylthio)-3-thiapentane, 1,6-bis(2,3-epithiopropylthio)hexane, 1,6-bis(2,3-epithiopropylthio)-2-methylhexane, 3,8-bis(2,3-epithiopropylthio)-3,6-dithiaoctane, 1,2,3-tris(2,3-epithiopropylthio)propane, 2,2-bis(2,3-epithiopropylthio)-1,3-bis(2,3-epithiopropylthiomethyl)propane, 2,2-bis(2,3-epithiopropylthiomethyl)-1-(2,3-epithiopropylthio)butane, 1,5-bis(2,3-epithiopropylthio)-2-(2,3-epithiopropylthiomethyl)-3-thiapentane, 1,5-bis(2,3-epithiopropylthio)-2,4-bis(2,3-epithiopropylthiomethyl)-3-thiapentane, 1-(2,3-epithiopropylthio)-2,2-bis(2,3-epithiopropylthiomethyl)-4-thiahexane, 1,5,6-tris(2,3-epithiopropylthio)-4-(2,3-epithiopropylthiomethyl)-3-thiahexane, 1,8-bis(2,3-epithiopropylthio)-4-(2,3-epithiopropylthiomethyl)-3,6-dithiaoctane, 1,8-bis(2,3-epithiopropylthio)-4,5-bis(2,3-epithiopropylthiomethyl)-3,6-dithiaoctane, 1,8-bis(2,3-epithiopropylthio)-4,4-bis(2,3-epithiopropylthiomethyl)-3,6-dithiaoctane, 1,8-bis(2,3-epithiopropylthio)-2,5-bis(2,3- epithiopropylthiomethyl)-3,6-dithiaoctane, 1,8-bis(2,3-epithiopropylthio)-2,4,5-tris(2,3-epithiopropylthiomethyl)-3,6-dithiaoctane, 1,1,1-tris[[2-(2,3-epithiopropylthio)ethyl]thiomethyl]-2-(2,3-epithiopropylthio)ethane, 1,1,2,2-tetrakis[[2-(2,3-epithiopropylthio)ethyl]thiomethyl]ethane, 1,11-bis(2,3-epithiopropylthio)-4,8-bis(2,3-epithiopropylthiomethyl)-3,6,9-trithiaundecane, 1,11-bis(2,3-epithiopropylthio)-4,7-bis(2,3-epithiopropylthiomethyl)-3,6,9-trithiaundecane, 1,11-bis(2,3-epithiopropylthio)-5,7-bis(2,3-epithiopropylthiomethyl)-3,6,9-trithiaundecane and the like;

cyclic aliphatic 2,3-epithiopropylthio compounds such as 1,3-bis(2,3-epithiopropylthio)cyclohexane, 1,4-bis(2,3-epithiopropylthio)cyclohexane, 1,3-bis(2,3-epithiopropylthiomethyl)cyclohexane, 1,4-bis(2,3-epithiopropylthiomethyl)cyclohexane, 2,5-bis(2,3-epithiopropylthiomethyl)-1,4-dithiane, 2,5-bis[[2-(2,3-epithiopropylthio)ethyl]thiomethyl]-1,4-dithiane, 2,5-bis(2,3-epithiopropylthiomethyl)-2,5-dimethyl-1,4-dithiane and the like;

aromatic 2,3-epithiopropylthio compounds such as 1,2-bis(2,3-epithiopropylthio)benzene, 1,3-bis(2,3-epithiopropylthio)benzene, 1,4-bis(2,3-epithiopropylthio)benzene, 1,2-bis(2,3-epithiopropylthiomethyl)benzene, 1,3-bis(2,3-epithiopropylthiomethyl)benzene, 1,4-bis(2,3-epithiopropylthiomethyl)benzene, bis[4-(2,3-epithiopropylthio)phenyl]methane, 2,2-bis[4-(2,3-epithiopropylthio)phenyl]propane, bis[4-(2,3-epithiopropylthio)phenyl]sulfide, bis[4-(2,3-epithiopropylthio)phenyl]sulfone, 4,4'-bis(2,3-epithiopropylthio)biphenyl and the like;

compounds each having one epithio group such as ethylene sulfide, propylene sulfide, mercaptopropylene sulfide, mercaptobutene sulfide, epithiochlorohydrin and the like;

chained aliphatic 2,3-epithiopropyloxy compounds such as bis(2,3-epithiopropyl)ether, bis(2,3-epithiopropyloxy)methane, 1,2-bis(2,3-epithiopropyloxy)ethane, 1,2-bis(2,3-epithiopropyloxy)propane, 1,3-bis(2,3-epithiopropyloxy)propane, 1,3-bis(2,3-epithiopropyloxy)-2-methylpropane, 1,4-bis(2,3-epithiopropyloxy)butane, 1,4-bis(2,3-epithiopropyloxy)-2-methylbutane, 1,3-bis(2,3-epithiopropyloxy)butane, 1,5-bis(2,3-epithiopropyloxy)pentane, 1,5-bis(2,3-epithiopropyloxy)-2-methylpentane, 1,5-bis(2,3-epithiopropyloxy)-3-thiapentane, 1,6-bis(2,3-epithiopropyloxy)hexane, 1,6-bis(2,3-epithiopropyloxy)-2-methylhexane, 3,8-bis(2,3-epithiopropyloxy)-3,6-dithiaoctane, 1,2,3-tris(2,3-epithiopropyloxy)propane, 2,2-bis(2,3-epithiopropyloxy)-1,3-bis(2,3-epithiopropyloxymethyl)propane, 2,2-bis(2,3-epithiopropyloxymethyl)-1-(2,3-epithiopropyloxy)butane, 1,5-bis(2,3-epithiopropyloxy)-2-(2,3-epithiopropyloxymethyl)-3-thiapentane, 1,5-bis(2,3-epithiopropyloxy)-2,4-bis(2,3-epithiopropyloxymethyl)-3-thiapentane, 1-(2,3-epithiopropyloxy)-2,2-bis(2,3-epithiopropyloxymethyl)-4-thiahexane, 1,5,6-tris(2,3-epithiopropyloxy)-4-(2,3-epithiopropyloxymethyl-3-thiahexane, 1,8-bis(2,3-epithiopropyloxy)-4-(2,3-epithiopropyloxymethyl)-3,6-dithiaoctane, 1,8-bis(2,3-epithiopropyloxy)-4,5-bis(2,3-epithiopropyloxymethyl)-3,6-dithiaoctane, 1,8-bis(2,3-epithiopropyloxy)-4,4-bis(2,3-epithiopropyloxymethyl)-3,6-dithiaoctane, 1,8-bis(2,3-epithiopropyloxy)-2,5-bis(2,3-epithiopropyloxymethyl)-3,6-dithiaoctane, 1,8-bis(2,3-epithiopropyloxy)-2,4,5-tris(2,3-epithiopropyloxymethyl)-3,6-dithiaoctane, 1,1,1-tris[[2-(2,3-epithiopropyloxy)ethyl]thiomethyl]-2-(2,3-epithiopropyloxy)ethane, 1,1,2,2-tetrakis[[2-(2,3-epithiopropyloxy)ethyl]thiomethyl]ethane, 1,11-bis(2,3-epithiopropyloxy)-4,8-bis(2,3-epithiopropyloxymethyl)-3,6,9-trithiaundecane, 1,11-bis(2,3-epithiopropyloxy)-4,7-bis(2,3-epithiopropyloxymethyl)-3,6,9-trithiaundecane, 1,11-bis(2,3-epithiopropyloxy)-5,7-bis(2,3-epithiopropyloxymethyl)-3,6,9-trithiaundecane and the like;

cyclic aliphatic 2,3-epithiopropyloxy compounds such as 1,3-bis(2,3-epithiopropyloxy)cyclohexane, 1,4-bis(2,3-epithiopropyloxy)cyclohexane, 1,3-bis(2,3-epithiopropyloxymethyl)cyclohexane, 1,4-bis(2,3-epithiopropyloxymethyl)cyclohexane, 2,5-bis(2,3-epithiopropyloxymethyl)-1,4-dithiane, 2,5-bis[[2-(2,3-epithiopropyloxy)ethyl]thiomethyl]-1,4-dithiane, 2,5-bis(2,3-epithiopropyloxymethyl)-2,5-dimethyl-1,4-dithiane and the like; and aromatic 2,3-epithiopropyloxy compounds such as 1,2-bis(2,3-epithiopropyloxy)benzene, 1,3-bis(2,3-epithiopropyloxy)benzene, 1,4-bis(2,3-epithiopropyloxy)benzene, 1,2-bis(2,3-epithiopropyloxymethyl)benzene, 1,3-bis(2,3-epithiopropyloxymethyl)benzene, 1,4-bis(2,3-epithiopropyloxymethyl)benzene, bis[4-(2,3-epithiopropyloxy)phenyl]methane, 2,2-bis[4-(2,3-epithiopropyloxy)phenyl]propane, bis[4-(2,3-epithiopropyloxy)phenyl]sulfide, bis[4-(2,3-epithiopropyloxy)phenyl]sulfone, 4,4'-bis(2,3-epithiopropyloxy)biphenyl and the like, but are not restricted to these exemplified compounds alone.

Of these exemplified compounds, preferable examples of the compound include bis(1,2-epithioethyl)sulfide, bis(1,2-epithioethyl)disulfide, bis(2,3-epithiopropyl)sulfide, bis(2,3-epithiopropylthio)methane and bis(2,3-epithiopropyl)disulfide. More preferable examples thereof include bis(1,2-epithioethyl)sulfide, bis(1,2-epithioethyl)disulfide, bis(2,3-epithiopropyl)sulfide and bis(2,3-epithiopropyl)disulfide. Further more preferable examples thereof include bis(2,3-epithiopropyl)sulfide and bis(2,3-epithiopropyl)disulfide.

Specifically, as an active hydrogen compound to be added to the aforementioned epithio compound, thiol compounds, preferably 5,7-dimercaptomethyl-1,11-dimercapto-3,6,9-trithiaundecane, 4,7-dimercaptomethyl-1,11-dimercapto-3,6,9-trithiaundecane, 4,8-dimercaptomethyl-1,11-dimercapto-3,6,9-trithiaundecane and the like, can be used in combination thereof.

Thietane Compound

As a thietane compound, a metal-containing thietane compound or a non-metal thietane compound can be used.

Examples of the metal thietane compound include alkylthio(thietanylthio)tin such as methylthio tris(thietanylthio)tin, ethylthio tris(thietanylthio)tin, propylthio tris(thietanylthio)tin, isopropylthio tris(thietanylthio)tin and the like;

bis(alkylthio)bis(thietanylthio)tin such as bis(methylthio)bis(thietanylthio)tin, bis(ethylthio)bis(thietanylthio)tin, bis(propylthio)bis(thietanylthio)tin, bis(isopropylthio)bis(thietanylthio)tin and the like;

alkylthio(alkylthio)bis(thietanylthio)tin such as ethylthio(methylthio)bis(thietanylthio)tin, methylthio(propylthio)bis(thietanylthio)tin, isopropylthio(methylthio)bis(thietanylthio)tin, ethylthio(propylthio)bis(thietanylthio)tin, ethylthio(isopropylthio)bis(thietanylthio)tin, isopropylthio(propylthio)bis(thietanylthio)tin and the like;

bis(thietanylthio) cyclic dithiotin compounds such as bis(thietanylthio)dithiastannetane, bis(thietanylthio)dithiastannolane, bis(thietanylthio)dithiastanninane, bis(thietanylthio)trithiastannocane and the like;

alkyl(thietanylthio)tin compounds such as methyltris(thietanylthio)tin, dimethylbis(thietanylthio)tin, butyltris(thietanylthio)tin and the like; and metal thietane compounds such as tetrakis(thietanylthio)tin, tetrakis(thietanylthio)germanium, tris(thietanylthio)bismuth, tris(thietanylthio)antimony and the like.

Furthermore, examples of the non-metal thietane compound include bisthietanyl disulfide, bisthietanyl tetrasulfide, bis(thietanylthio)methane, 3-(((thietanylthio)methylthio)methylthio)thiethane and the like.

A more preferable example includes tetrakis(thietanylthio)tin.

Specifically, as an active hydrogen compound to be added to the aforementioned metal thietane compound, thiol compounds, preferably 4-mercaptomethyl-1,8-dimercapto-3,6-dithiaoctane, 3-mercaptothietane and the like, can be used in combination thereof.

In the composition of the present invention, the proportion of each component constituting the composition is not particularly limited; however it is preferably as follows.

The content of the aforementioned product is not particularly limited; however it is usually not less than 5 weight %, preferably not less than 10 weight %, more preferably not less than 30 weight %, and further preferably not less than 50 weight %, based on the total weight of the composition of the present invention.

Furthermore, the composition of the present invention may further contain, if necessary, a known or publicly used polymerization catalyst in order to control the polymerization rate.

Furthermore, the composition of the present invention may contain, if necessary, a bluing agent. The bluing agent has an absorption band in an orange-yellow wavelength range of the visible light region, and has a function of adjusting the color tone of the resin. The bluing agent further specifically contains a substance exhibiting colors from blue to violet.

The bluing agent used for the composition of the present invention is not particularly limited, and concrete examples thereof include a dye, a fluorescent whitening agent, a fluorescent pigment, an inorganic pigment and the like. The bluing agent is suitably selected from those which can be used as a bluing agent according to the physical properties required for a lens, the color tone of the resin or the like. These bluing agents may be used singly or two or more kinds may be used in combination.

Of these bluing agents, a dye is preferred from the viewpoints of the solubility into the composition and the transparency of the obtained resin. Of dyes, preferably used is a dye containing one or two or more kinds selected from blue based dyes and violet based dyes, however it may be mixed with other color based dyes depending on the situation. For example, gray, brown, red and orange based dyes can also be used in addition to the blue and violet based dyes. Concrete examples of a combination of such bluing agents include a combination of a blue based dye with a red based dye, a combination of a violet based dye with a red based dye, and the like.

From the viewpoint of the absorption wavelength, the maximum absorption wavelength of the dye is preferably not less than 520 and not more than 600 nm and further preferably not less than 540 and not more than 580 nm.

From the viewpoint of the structure of the compound, an anthraquinone based dye is preferable.

Concrete examples of the dye include PS Blue RR, PS Violet RC, PET Blue 2000, PS Brilliant Red HEY, MLP RED V-1 (product names manufactured by DyStar Japan Ltd.) and the like.

The amount of the bluing agent used is different depending on the kind of monomer, existence of various additives in use, the kind and amount of additives in use, the polymerization method or polymerization conditions. The amount is generally not less than 0.001 and not more than 500 ppm, preferably not less than 0.005 and not more than 100 ppm and further preferably not less than 0.01 and not more than 10 ppm, based on the total amount of monomers, namely, the total weight of the polymerizable compound contained in the composition. When the amount of the bluing agent added is excessively high, the entire lens becomes excessively blue in some cases; therefore, it is not preferable. Further, when it is excessively small, the effect of improvement of color tone is not fully exhibited in some cases; therefore, it is not preferable.

A method for adding a bluing agent is not particularly limited, and the bluing agent is preferably added to monomers in advance. As a method, there can be adopted various methods such as a method including dissolving the bluing agent in a monomer, or a method including preparing a master solution containing a high density bluing agent and adding it by diluting with a monomer using the master solution or other additives.

Furthermore, in some cases, in order to obtain a good resin, a method or operation generally used for synthesizing an organic compound, such as purification, cleaning, hot insulation, cold insulation, filtration, reduced-pressure treatment or the like is preferably performed for the composition of the present invention, or a known compound is preferably added as a stabilizer or a resin modifier for improving a resin and handling property, for example, for controlling the optical physical properties such as the refractive index, Abbe's number and the like, physical properties such as color tone, light resistance, weather resistance, heat resistance, impact resistance, hardness, specific gravity, linear expansion coefficient, polymerization shrinkability, water absorption, hygroscopicity, chemical resistance, viscoelasticity and the like, and transmittance and transparency of a resin produced by curing the composition, and controlling the viscosity of the composition, and preservation and transport handling property. Examples of the compound added for improving stability such as long-term preservation stability, polymerization stability and thermal stability include a polymerization retardant, a polymerization inhibitor, a deoxidant, an antioxidant and the like.

Purification of the composition is a means used for improving the transparency of the resin obtained by curing, improving the color tone or increasing the purity of the resin. As a method for purifying the composition of the present invention, any known method, for example, recrystallization, column chromatography (a silica gel method, an activated carbon method, an ion-exchange resin method or the like), extraction or the like, may be performed with any timing as long as the transparency and color tone of the resin obtained by curing the purified composition are generally improved.

A method for cleaning the composition is a means used for improving the transparency and color tone of the resin obtained by curing. Such a method may be conducted at timing when or after the synthesized composition is taken out. In this method, the composition is washed with a polar and/or nonpolar solvent to remove or reduce a resin transparency inhibitor, for example, an inorganic salt used for synthesizing the composition or by-produced in synthesizing the composition, such as an ammonium salt or the like. Although the solvent used depends on the composition to be cleaned and the polarity of a solution containing the composition, and is not limited, a solvent which can dissolve a component to be removed, and which is hardly compatible with the composition to be cleaned and the solution containing the composition is preferably used. The solvent may be used singly, or a mixture of two or more solvents may be used. Although the amount of a component to be removed depends on the purpose and application, the amount is preferably as low as possible. The amount is usually not more than 5,000 ppm and more preferably not more than 1,000 ppm. In this case, good results are produced in some cases.

A hot insulation, cold insulation or filtration method for the composition is a means used for improving the transparency or color tone of the resin obtained by curing. Such a method is generally conducted at timing when or after the synthesized composition is taken out. In the hot insulation method, for example, when the composition is crystallized to deteriorate handling property during storage, the composition is melted by heating within a range causing no deterioration in the performance of the composition and the resin obtained by curing the composition. Although the heating temperature range and heat melting method depend on the structure of the compound constituting the composition to be handled and are not limited, the heating temperature is generally in a range of the solidification point +50 degrees centigrade and preferably the solidification point +20 degrees centigrade. In this method, the composition may be melted by mechanically stirring with a stirring device or bubbling with an inert gas for moving an internal liquid. The cold insulation method is generally performed for improving the preservation stability of the composition. However, when the composition has a high melting point, consideration may be given to the storage temperature to improve handling property after crystallization. Although the cold insulation temperature depends on the structure and preservation stability of the compound constituting the composition to be handled, and is not limited, the composition of the present invention needs to be stored at a temperature or below which can maintain the stability thereof.

The composition of the present invention used for optical applications is required to have excessively high transparency, and thus the composition may be usually filtered with a filter having a small pore size. Although the pore size of the filter used herein is usually not less than 0.05 μm and not more than 10 μm, the pore size is preferably not less than 0.05 μm and not more than 5 μm and more preferably not less than 0.1 μm and not more than 5 μm from the viewpoints of operationality and performance. In many cases, filtration of the composition of the present invention produces good results without exception. Although a low filtration temperature near the solidification temperature produces more desirable results in some cases, filtration is preferably performed at a temperature causing no trouble in the filtration work when solidification proceeds during filtration in some cases.

The reduced-pressure treatment is a means for removing a solvent, dissolved gas and odor which deteriorate the performance of the resin generally produced by curing the composition. Since a dissolved solvent generally decreases the refractive index of the resultant resin and deteriorates the heat resistance thereof, the dissolved solvent may be removed as much as possible. Although the allowable amount of the dissolved solvent depends on the structure of the compound constituting the composition to be handled and the structure of the dissolved solvent, and is not limited, the allowable amount is usually preferably not more than 1% and more preferably not more than 5,000 ppm. The dissolved gas inhibits polymerization or causes the problem of mixing bubbles in the resultant resin, and is thus preferably removed.

Particularly, a moisture gas such as water vapor or the like is preferably removed by bubbling with a dry gas. The amount of the dissolved gas can be determined depending on the structure of the compound constituting the composition, and the physical properties, structure and kind of the dissolved gas.

As a method for producing the composition according to the present invention, a mixture of the aforementioned product (product obtained by the reaction of an Sb or Bi oxide or an Sb or Bi halide with at least one kind of polythiol compounds selected from compounds having at least two thiol groups in a molecule) and, if necessary, the aforementioned various other polymerizable compounds, a polymerization catalyst, an additive and the like introduced thereinto all at once may be typically melted by heating and mixed.

The resultant composition is useful, for example, as a raw material monomer composition for use in a transparent resin having an extremely high refractive index.

Furthermore, the resultant composition can be polymerized and cured.

The kind and amount of the polymerization catalyst used for obtaining a cured resin, and the kind and ratio of the monomer are determined depending on the structure of the compound constituting the composition.

In curing and molding the composition of the present invention, according to purposes, in the same manner as a known molding method, various substances, such as a stabilizer, a resin modifier, a chain extender, a cross-linking agent, a light stabilizer including a typical hindered amine light stabilizer (HALS), an ultraviolet absorber including a typical benzotriazole ultraviolet absorber, an antioxidant including a typical hindered phenolic antioxidant, a coloring inhibitor, a filler, an external mold releasing agent including a typical silicone type external mold releasing agent, or an internal mold releasing agent including typically acidic phosphate, and a surface active agent such as quaternary ammonium salt, quaternary phosphonium salt internal mold releasing agent or the like, an adhesion improving agent and the like may be added. Herein, the internal mold releasing agent includes those catalysts exhibiting the mold release effect among the aforementioned various catalysts.

Although the amount of each of the aforementioned various additives which can be added is different depending on the kind, structure and effect of each additive, and is not limited, the adding amount is usually in the range of not less than 0.001 and not more than 10 weight % and preferably in the range of not less than 0.01 and not more than 5 weight %, based on the total weight of the composition. Within these ranges, a sufficiently cured resin can be produced, and the obtained resin has good transparency and optical physical properties in some cases.

For example, when a hindered amine light stabilizer (HALS) and a phenolic antioxidant, a phosphite type antioxidant or a thioether type antioxidant are added, the color tone of the resin is improved in some cases. In particular, when a hindered amine light stabilizer (HALS) is added, the color tone of the resin is greatly improved in some cases. Examples of the hindered amine light stabilizer (HALS) include ADK STAB LA-77, LA-57, LA-52, LA-67, LA-62, LA-68, LA-63, LA-87, LA-82 and the like manufactured by ADEKA Corporation, but are not restricted thereto.

The resin is obtained by polymerization of the aforementioned composition. Examples of the polymerization method include various known methods used when producing plastic lenses. A typical method includes a casting polymerization.

When casting polymerization of the composition of the present invention is carried out, the composition is degassed under reduced pressure or filtered off using a filter as required, and then the composition is poured into a mold, and if necessary, heated for carrying out polymerization. In this case, it is preferable to carry out polymerization by slowly heating from a low temperature to a high temperature.

The aforementioned mold is composed of, for example, two pieces of mirror surface-ground molds via a gasket made of polyethylene, an ethylene vinyl acetate copolymer, polyvinyl chloride and the like. Typical examples of the mold include, though not restricted to, combined molds such as glass and glass, glass and plastic plate, glass and metal plate, and the like. The mold may comprise two pieces of molds fixed by a tape such as a polyester adhesive tape or the like. In addition, a known method such as the mold release process may be performed for the mold, as needed.

When carrying out casting polymerization, the polymerization temperature is affected by the polymerization conditions such as the kind of the polymerization initiator and the like, and is not limited. However, it is usually not less than −50 and not more than 200 degrees centigrade, preferably not less than −20 and not more than 170 degrees centigrade, and more preferably not less than 0 and not more than 150 degrees centigrade.

The polymerization time is affected by the polymerization temperature; however it is usually not less than 0.01 and not more than 200 hours and preferably not less than 0.05 and not more than 100 hours. Polymerization can also be carried out in combination of several temperatures by conducting fixed temperature, temperature elevation, temperature dropping and the like as required.

Furthermore, the composition of the present invention can also be polymerized by applying the active energy line such as an electron beam, ultraviolet light, visible light or the like. At this time, a radical polymerization catalyst or a cationic polymerization catalyst for initiating polymerization by the active energy line is used as required.

After the thus-obtained resin is cured, it may be subjected to an annealing process as required. Furthermore, for purposes of anti-reflection, high hardness grant, wear resistance improvement, anti-fogging property grant or fashionability grant, various known physical or chemical processes such as surface polishing, antistatic process, hard coat process, non-reflective coat process, dyeing process, photochromic process (for example, photochromic lens process and the like) and the like may be performed as needed.

The resin obtained by polymerization of the composition of the present invention has high transparency, good heat resistance and mechanical strength, while attaining a high refractive index. So, the resin is useful, for example, as a resin for use in optical components such as plastic lenses and the like.

Examples of the optical component include various plastic lenses such as a spectacle lens for vision correction, a lens for cameras, a fresnel lens for liquid crystal projectors, a lenticular lens, a contact lens and the like; a sealing material for light emitting diodes (LED); an optical waveguide; an optical adhesive used for the junction of an optical lens and an optical waveguide; an anti-reflection film to be used for optical lenses; and a transparent coating or transparent substrate used for a liquid crystal display member such as a substrate, a light guiding plate, a film, a sheet and the like.

EXAMPLES

The present invention is now illustrated below with reference to Examples.

The physical properties of the resins or optical components (lenses) produced in the following Examples were evaluated in the following manner.

Transparency: It was visually confirmed using a slide projector.

Refractive index: It was measured at 20 degree centigrade using a Pulfrich refractometer.

Heat resistance: Tg (degree centigrade) of the TMA penetration method (load: 50 g, pinpoint: 0.5 mmΦ, temperature elevation rate: 10 degree centigrade/min) was measured as heat resistance.

Example 1

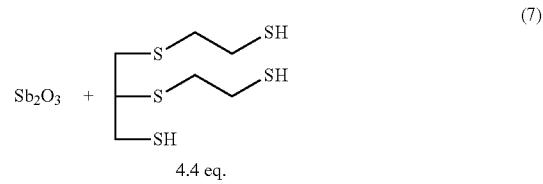 [SMILES: "Sb2O3" ; SCCSCC(CS)SCCS]

Into a reactor were introduced 4-mercaptomethyl-1,8-dimercapto-3,6-dithiaoctane (80 g; 307 mmole), and antimony trioxide (20 g; 69 mmole) [charging molar ratio: metal/polythiol=1/4.4], and then acetic acid (2 g) was further introduced thereinto. The resulting mixture was slowly heated for carrying out the reaction at 70 degrees centigrade for 24 hours. The reaction mixture was cooled, and then methanol was added and stirred. Decantation was repeatedly carried out three times for removing by-produced water and acetic acid. The resultant oily product was dried under reduced pressure to obtain 94 g (quantitatively) of a desired product (the reaction formula represented by the above formula (7)). The analysis results of the desired product are shown below.

IR (Universal ATR method): 692, 832, 1198, 1256, 1411, 2530 (SH group), 2902 $cm^{-1}$.

Elemental Analysis Measurement Value C, 27.0%, H, 4.4%, Sb: 16.4%.

Example 2

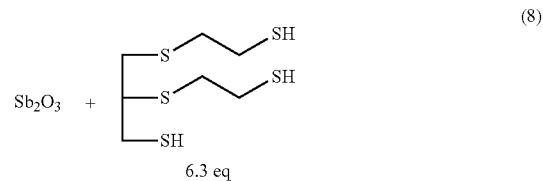 [SMILES: "Sb2O3" ; SCCSCC(CS)SCCS]

Into a reactor were introduced 4-mercaptomethyl-1,8-dimercapto-3,6-dithiaoctane (28 g; 107 mmole) and antimony trioxide (5 g; 17 mmole) [charging molar ratio: metal/polythiol=1/6.3], and then acetic acid (0.75 g) was further introduced thereinto. The resulting mixture was slowly heated for carrying out the reaction at 70 degrees centigrade for 10 hours. Post-treatment was carried out in the same manner as in Example 1 to obtain 31 g (quantitatively) of a desired product (the reaction formula represented by the above formula (8)). The analysis results of the desired product are shown below.

IR (Universal ATR method): 692, 833, 1206, 1261, 1412, 2533 (SH group), 2904 $cm^{-1}$.

Elemental Analysis Measurement Value C, 28.4%; H: 4.9%; Sb, 12.4%.

Example 3

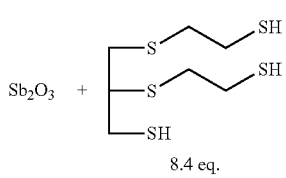

(9)

Into a reactor were introduced 4-mercaptomethyl-1,8-dimercapto-3,6-dithiaoctane (28 g; 107 mmole) and antimony trioxide (3.75 g; 12.8 mmole) [charging molar ratio: metal/polythiol=1/8.4], and then acetic acid (0.75 g) was further introduced thereinto. The resulting mixture was slowly heated for carrying out the reaction at 70 degrees centigrade for 10 hours. Post-treatment was carried out in the same manner as in Example 1 to obtain 30 g (quantitatively) of a desired product (the reaction formula represented by the above formula (9)). The analysis results of the desired product are shown below.

IR (Universal ATR method): 693, 833, 1206, 1262, 1413, 2534 (SH group), 2906 cm$^{-1}$.

Elemental Analysis: Measurement Value C, 29.3%; H, 5.4%; Sb, 9.6%.

Example 4

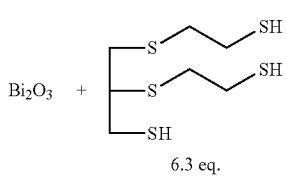

(10)

Into a reactor were introduced 4-mercaptomethyl-1,8-dimercapto-3,6-dithiaoctane (28 g; 107 mmole) and bismuth oxide (III) (8 g; 17 mmole) [charging molar ratio: metal/polythiol=1/6.3], and then acetic acid (0.75 g) was further introduced thereinto. The resulting mixture was slowly heated for carrying out the reaction at 70 degrees centigrade for 10 hours. Post-treatment was carried out in the same manner as in Example 1 to obtain 33 g (yield: 98%) of a desired product (the reaction formula represented by the above formula (10)). The analysis results of the desired product are shown below.

IR (Universal ATR method): 693, 833, 1206, 1260, 1411, 2529 (SH group), 2902 cm$^{-1}$.

Elemental Analysis: Measurement Value C, 26.0%; H, 4.4%; Bi, 20.0%.

Example 5

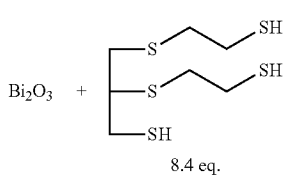

(11)

Into a reactor were introduced 4-mercaptomethyl-1,8-dimercapto-3,6-dithiaoctane (28 g; 107 mmole) and bismuth oxide (III) (6 g; 12.8 mmole) [charging molar ratio: metal/polythiol=1/8.4], and then acetic acid (0.75 g) was further introduced thereinto. The resulting mixture was slowly heated for carrying out the reaction at 70 degrees centigrade for 10 hours. The reaction mixture was cooled, and then methanol was added thereto. Decantation was carried out, and the oily product was dried under reduced pressure to obtain 32 g (quantitatively) of a desired product (the reaction formula represented by the above formula (11)). The analysis results of the desired product are shown below.

IR (Universal ATR method): 693, 833, 1207, 1262, 1412, 2530 (SH group), 2904 cm$^{-1}$.

Elemental Analysis: Measurement Value C, 27.3%; H, 4.9%; Bi, 16.6%.

Example 6

The refractive indexes (nD) of the products (desired products) obtained in Examples 1 to 3, 4 and 5 were measured at 20 degrees centigrade. The resultant physical property values are shown in Table 1.

Comparative Example 1

The refractive index (nD) of 4-mercaptomethyl-1,8-dimercapto-3,6-dithiaoctane was measured at 20 degrees centigrade. The resultant physical property values are shown in Table 1.

TABLE 1

|   | nD |
| --- | --- |
| Comparative Example 1: thiol compound (A) | 1.63 |
| Example 1 | 1.74 |
| Example 2 | 1.71 |
| Example 3 | 1.69 |
| Example 4 | 1.73 |
| Example 5 | 1.70 |

Thiol Compound (A)

4-mercaptomethyl-1,8-dimercapto-3,6-dithiaoctane

It was found that the refractive indexes in Examples 1 to 5 were higher as compared to Comparative Example 1.

Example 7

To the product (desired product) (15 weight parts) obtained in Example 1 was added 4-mercaptomethyl-1,8-dimercapto-3,6-dithiaoctane (36 weight parts), and a mixture (49 weight parts) of 2,5-bis(isocyanatomethyl)-bicyclo[2.2.1]heptane and 2,6-bis(isocyanatomethyl)-bicyclo[2.2.1]heptane was further mixed to give a homogeneous solution. This mixed solution was degassed under reduced pressure for 10 minutes, and then poured in a mold equipped with a glass mold and tapes. This mold was put into a polymerization oven, and then gradually heated from 25 to 120 degrees centigrade over a period of 24 hours to conduct polymerization. After completion of the polymerization, the mold was taken out from the oven, and the molded product was released from the mold.

The physical property values of the resultant molded product are shown in Table 2.

Examples 8 to 12

A mixed solution and a molded product were respectively produced in the same manner as in Example 7, except for using compositions of Table 2. The physical property values of the resultant molded products are shown in Table 2. Examples 1 to 3 in Table 2 refer to the products (desired products) obtained in respective Examples.

Incidentally, in respective Examples and Comparative Examples, transparency (appearance) was visually confirmed. The refractive index and Abbe's number were measured at 20 degree centigrade using a Pulfrich refractometer. Heat resistance was measured by the TMA (Thermal Mechanical Analysis) penetration method. In Examples and Comparative Examples to be described below, they were measured in the same manner.

TABLE 2

| | Composition (weight parts) | | | | |
|---|---|---|---|---|---|
| | Example 1 | Example 2 | Example 3 | Thiol compound (A) | Isocyanate compound (C) |
| Comp. Example 2 | 0 | 0 | 0 | 46 | 54 |
| Example 7 | 15 | 0 | 0 | 36 | 49 |
| Example 8 | 22 | 0 | 0 | 31 | 47 |
| Example 9 | 31 | 0 | 0 | 25 | 44 |
| Example 10 | 59 | 0 | 0 | 16 | 25 |
| Example 11 | 0 | 60 | 0 | 0 | 40 |
| Example 12 | 0 | 0 | 55 | 0 | 45 |

| | Polymerization Catalyst ppm | Optical Physical Property Refractive Index (ne) | Abbe's Number (ve) | Transparency | Heat Resistance Tg (° C.) |
|---|---|---|---|---|---|
| Comp. Example 2 | x 230 | 1.623 | 38 | Transparent | 113 |
| Example 7 | No | 1.636 | 36 | Transparent | 120 |
| Example 8 | No | 1.641 | 35 | Transparent | 113 |
| Example 9 | No | 1.651 | 33 | Transparent | 118 |
| Example 10 | No | 1.691 | 30 | Transparent | ND |
| Example 11 | No | 1.667 | 31 | Transparent | 110 |
| Example 12 | No | 1.652 | 33 | Transparent | 109 |

Thiol compound (A): 4-mercaptomethyl-1,8-dimercapto-3,6-dithiaoctane
Isocyanate compound (C): bis(isocyanatomethyl)bicyclo[2.2.1]heptane
x: dibutyltin dichloride

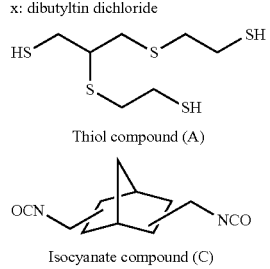

Thiol compound (A)

Isocyanate compound (C)

Examples 13 and 14

A mixed solution and a molded product were respectively produced in the same manner as in Example 7, except for using compositions of Table 3. The physical property values of the resultant molded products are shown in Table 3. Examples 4 and 5 in Table 3 refer to the products (desired products) obtained in respective Examples.

TABLE 3

| | Composition (weight parts) | | | |
|---|---|---|---|---|
| | Example 4 | Example 5 | Thiol compound (A) | Isocyanate compound (C) |
| Example 13 | 43 | 0 | 24 | 43 |
| Example 14 | 0 | 62 | 0 | 33 |

| | Polymerization Catalyst ppm | Optical Physical Property Refractive Index (ne) | Abbe's Number (ve) | Transparency | Heat Resistance Tg (° C.) |
|---|---|---|---|---|---|
| Example 13 | No | 1.652 | 31 | Transparent | 108 |
| Example 14 | No | 1.671 | 30 | Transparent | 96 |

Thiol compound (A): 4-mercaptomethyl-1,8-dimercapto-3,6-dithiaoctane
Isocyanate compound (C): bis(isocyanatomethyl)bicyclo[2.2.1]heptane
x: dibutyltin dichloride

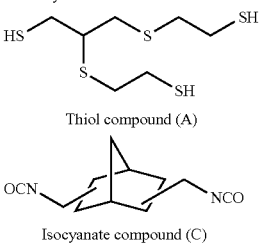

Thiol compound (A)

Isocyanate compound (C)

Comparative Example 2

4-mercaptomethyl-1,8-dimercapto-3,6-dithiaoctane (46 weight parts), a mixture (54 weight parts) of 2,5-bis(isocyanatomethyl)-bicyclo[2.2.1]heptane and 2,6-bis(isocyanatomethyl)-bicyclo[2.2.1]heptane, and dibutyltin dichloride (230 ppm) were mixed to give a homogeneous solution. This mixed solution was degassed under reduced pressure for 10 minutes, and then poured in a mold equipped with a glass mold and tapes. This mold was put into a polymerization oven, and then gradually heated from 25 to 120 degrees centigrade over a period of 40 hours to conduct polymerization. After completion of the polymerization, the mold was taken out from the oven, and the molded product was released from the mold.

The physical property values of the resultant molded product are shown in Table 2.

As clear from Tables 2 and 3, it was found that the refractive indexes of Examples 7 to 14 were rather higher than that of Comparative Example 2.

Example 15

To the product (desired product) (28 weight parts) obtained in Example 2 was added 4-mercaptomethyl-1,8-dimercapto-3,6-dithiaoctane (28 weight parts), and m-xylylene diisocyanate (44 weight parts) was further mixed to give a homogeneous solution. This mixed solution was degassed under reduced pressure for 10 minutes, and then poured in a mold equipped with a glass mold and tapes. This mold was put into a polymerization oven, and then gradually heated from 25 to 120 degrees centigrade over a period of 40 hours to conduct polymerization. After completion of the polymerization, the mold was taken out from the oven, and the molded product was released from the mold.

The physical property values of the resultant molded product are shown in Table 4.

Examples 16 to 19

A mixed solution and a molded product were respectively produced in the same manner as in Example 15, except for using compositions of Table 4. The physical property values of the resultant molded products are shown in Table 4.

Comparative Example 3

4-mercaptomethyl-1,8-dimercapto-3,6-dithiaoctane (48 weight parts), m-xylylene diisocyanate (52 weight parts) and dibutyltin dichloride (150 ppm) were mixed to give a homogeneous solution. This mixed solution was degassed under reduced pressure for 10 minutes, and then poured in a mold equipped with a glass mold and tapes. This mold was put into a polymerization oven, and then gradually heated from 25 to 120 degrees centigrade over a period of 40 hours to conduct polymerization. After completion of the polymerization, the mold was taken out from the oven, and the molded product was released from the mold.

The physical property values of the resultant molded product are shown in Table 4.

TABLE 4

| | Composition (weight parts) | | | | |
|---|---|---|---|---|---|
| | Example 1 | Example 2 | Example 3 | Thiol compound (A) | Isocyanate compound (C) |
| Comp. Example 3 | 0 | 0 | 0 | 48 | 52 |
| Example 15 | 0 | 28 | 0 | 28 | 44 |
| Example 16 | 0 | 0 | 60 | 0 | 40 |
| Example 17 | 33 | 0 | 0 | 27 | 40 |
| Example 18 | 0 | 0 | 61 | 0 | 39 |
| Example 19 | 45 | 0 | 0 | 18 | 37 |

| | Polymerization Catalyst ppm | Optical Physical Property Refractive Index (ne) | Abbe's Number (ve) | Transparency | Heat Resistance Tg (° C.) |
|---|---|---|---|---|---|
| Comp. Example 3 | x 150 | 1.665 | 31 | Transparent | 85 |
| Example 15 | No | 1.681 | 29 | Transparent | 83 |
| Example 16 | No | 1.689 | 27 | Transparent | 84 |
| Example 17 | No | 1.690 | 27 | Transparent | 85 |
| Example 18 | No | 1.691 | 27 | Transparent | 76 |
| Example 19 | No | 1.698 | 27 | Transparent | 86 |

Thiol compound (A): 4-mercaptomethyl-1,8-dimercapto-3,6-dithiaoctane
Isocyanate compound (D): m-xylylene diisocyanate
x: dibutyltin dichloride

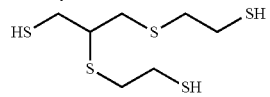

Thiol compound (A)

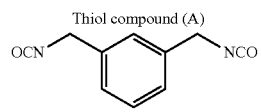

Isocyanate compound (D)

As clear from Table 4, it was found that the refractive indexes of Examples 15 to 19 were rather higher than that of Comparative Example 3.

Incidentally, Examples 1 to 3 in Table 4 refer to the products (desired products) obtained in respective Examples.

Example 20

To the product (desired product) (64 weight parts) of Example 2 was mixed butane-1,4-diisothiocyanate (a product of Lancaster; 36 weight parts) to give a homogeneous solution. This mixed solution was degassed under reduced pressure for 10 minutes, and then poured in a mold equipped with a glass mold and tapes. This mold was put into a polymerization oven, and then gradually heated from 25 to 120 degrees centigrade over a period of 24 hours to conduct polymerization. After completion of the polymerization, the mold was taken out from the oven, and the molded product was released from the mold.

The physical property values of the resultant molded product are shown in Table 5.

Example 21

A mixed solution and a molded product were produced in the same manner as in Example 20, except for using compositions of Table 5. The physical property values of the resultant molded product are shown in Table 5.

Comparative Example 4

4-mercaptomethyl-1,8-dimercapto-3,6-dithiaoctane (51 weight parts), dibutyltin dichloride (5000 ppm) and butane-1,4-diisothiocyanate (a product of Lancaster; 49 weight parts) were mixed to give a homogeneous solution. This mixed solution was degassed under reduced pressure for 10 minutes, and then poured in a mold equipped with a glass mold and tapes. This mold was put into a polymerization oven, and then gradually heated from 25 to 120 degrees centigrade over a period of 24 hours to conduct polymerization. After completion of the polymerization, the mold was taken out from the oven, and the molded product was released from the mold.

The physical property values of the resultant molded product are shown in Table 5.

TABLE 5

| | Composition (weight parts) | | | |
|---|---|---|---|---|
| | Example 2 | Example 3 | Thiol compound (A) | Isocyanate compound (E) |
| Comp. Example 4 | 0 | 0 | 51 | 49 |
| Example 20 | 64 | 0 | 0 | 36 |
| Example 21 | 0 | 60 | 0 | 40 |

| | Polymerization Catalyst ppm | Optical Physical Property Refractive Index (ne) | Abbe's Number (ve) | Transparency | Heat Resistance Tg (° C.) |
|---|---|---|---|---|---|
| Comp. Example 4 | x 5000 | 1.732 | 23 | Transparent | 51 |
| Example 20 | No | 1.763 | 22 | Transparent | 59 |

TABLE 5-continued

| Example 21 | No | 1.753 | 22 | Transparent | 56 |

Thiol compound (A): 4-mercaptomethyl-1,8-dimercapto-3,6-dithiaoctane
Isocyanate compound (E): butane-1,4-diisothiocyanate
x: dibutyltin dichloride

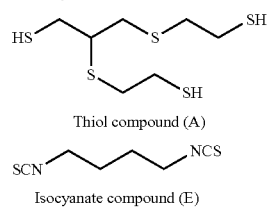

Thiol compound (A)

SCN~~~NCS

Isocyanate compound (E)

As clear from Table 5, it was found that the refractive indexes of Examples 20 and 21 were rather higher than that of Comparative Example 4.

Incidentally, Examples 2 and 3 in Table 5 refer to the products (desired products) obtained in respective Examples.

Example 22

To a mixture (6 weight parts) of 5,7-dimercaptomethyl-1,11-dimercapto-3,6,9-trithiaundecane, 4,7-dimercaptomethyl-1,11-dimercapto-3,6,9-trithiaundecane and 4,8-dimercaptomethyl-1,11-dimercapto-3,6,9-trithiaundecane were mixed N,N-dicyclohexylamine (800 ppm relative to the epithio compound), the product (desired product) (27 weight parts) obtained in Example 1 and bis(2,3-epithiopropyl)disulfane (66 weight parts) to obtain a homogeneous solution. The mixed solution was degassed under reduced pressure for 10 minutes, and then poured in a mold equipped with a glass mold and tapes. This mold was put into a polymerization oven, and then gradually heated from 30 to 120 degrees centigrade over a period of 24 hours to conduct polymerization. After completion of the polymerization, the mold was taken out from the oven, and the molded product was released from the mold.

The physical property values of the resultant molded product are shown in Table 6.

Comparative Example 5

To a mixture (10 weight parts) of 5,7-dimercaptomethyl-1,11-dimercapto-3,6,9-trithiaundecane, 4,7-dimercaptomethyl-1,11-dimercapto-3,6,9-trithiaundecane and 4,8-dimercaptomethyl-1,11-dimercapto-3,6,9-trithiaundecane were mixed N,N-dicyclohexylamine (1000 ppm relative to the epithio compound) and bis(2,3-epithiopropyl)disulfane (90 weight parts) to obtain a homogeneous solution. The mixed solution was degassed under reduced pressure for 10 minutes, and then poured in a mold equipped with a glass mold and tapes. This mold was put into a polymerization oven, and then gradually heated from 30 to 120 degrees centigrade over a period of 24 hours to conduct polymerization. After completion of the polymerization, the mold was taken out from the oven, and the molded product was released from the mold.

The physical property values of the resultant molded product are shown in Table 6.

TABLE 6

| | Composition (weight parts) | | |
|---|---|---|---|
| Example | Epithio compound (F) | Thiol compound (B) | |
| Comp. Example 5 | 0 | 90 | 10 |
| Example 22 | 27 | 66 | 6 |

| | Polymerization Catalyst ppm | Optical Physical Property Refractive Index (ne) | Abbe's Number (ve) | Transparency | Heat Resistance Tg (° C.) |
|---|---|---|---|---|---|
| Comp. Example 5 | Y | 1000 | 1.736 | 33 | Transparent | 73 |
| Example 22 | Y | 800 | 1.745 | 29 | Transparent | ND |

Thiol compound (B): Mixture of 5,7-dimercaptomethyl-1,11-dimercapto-3,6,9-trithiaundecane, 4,7-dimercaptomethyl-1,11-dimercapto-3,6,9-trithiaundecane and 4,8-dimercaptomethyl-1,11-dimercapto-3,6,9-trithiaundecane
Epithio compound (F): bis(2,3-epithiopropyl)disulfane
Y: N,N-dicyclohexylmethylamine

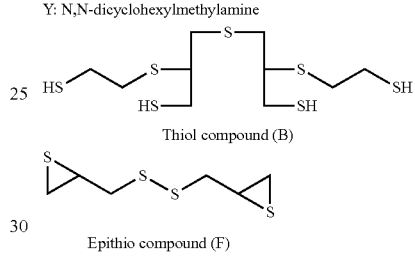

Thiol compound (B)

Epithio compound (F)

As clear from Table 6, it was found that the refractive index of Example 22 was rather higher than that of Comparative Example 5.

Incidentally, Example 1 in Table 6 refers to the product (desired product) obtained in Example 1.

Example 23

To the product (desired product) (5 weight parts) obtained in Example 1 was mixed tetrakis(3-thietanylthio) tin (95 weight parts), and the resulting mixture was melted by heating at 70 degrees centigrade to obtain a homogeneous solution. The mixed solution was degassed for 10 minutes, and then poured in a mold equipped with a glass mold and tapes. This mold was put into a polymerization oven, and then gradually heated from 75 to 130 degrees centigrade over a period of 48 hours to conduct polymerization. After completion of the polymerization, the mold was taken out from the oven, and the resin was released from the mold.

The physical property values of the resultant molded product are shown in Table 7.

Examples 24 and 25

A mixed solution and a molded product were respectively produced in the same manner as in Example 23, except for using compositions of Table 7. The physical property values of the resultant molded products are shown in Table 7.

Comparative Example 6

4-mercaptomethyl-1,8-dimercapto-3,6-dithiaoctane (10 weight parts) and tetrakis(3-thietanyl) tin (90 weight parts) were mixed and melted by heating at 70 degrees centigrade to obtain a homogeneous solution. The mixed solution was degassed for 10 minutes, and then poured in a mold equipped with a glass mold and tapes. This mold was put into a polymerization oven, and then gradually heated from 75 to 130 degrees centigrade over a period of 48 hours to conduct polymerization. After completion of the polymerization, the mold was taken out from the oven, and the resin was released from the mold.

The physical property values of the resultant molded product are shown in Table 7.

TABLE 7

| | Composition (weight parts) | | |
|---|---|---|---|
| Example 1 | Thiol compound (A) | | Metal thietane compound (G) |
| Comp. Example 6 | 0 | | 10 | 90 |
| Example 23 | 5 | | 0 | 95 |
| Example 24 | 10 | | 0 | 90 |
| Example 25 | 15 | | 0 | 85 |

| | Polymerization Catalyst ppm | Optical Physical Property Refractive Index (ne) | Abbe's Number (ve) | Transparency | Heat Resistance Tg (° C.) |
|---|---|---|---|---|---|
| Comp. Example 6 | No | 1.784 | 26 | Transparent | 123 |
| Example 23 | No | 1.798 | 25 | Transparent | 160 |
| Example 24 | No | 1.797 | 25 | Transparent | 139 |
| Example 25 | No | 1.789 | 24 | Transparent | 130 |

Thiol compound (A): 4-mercaptomethyl-1,8-dimercapto-3,6-dithiaoctane
Metal thietane compound (G): tetrakis (3-thietanylthio)tin

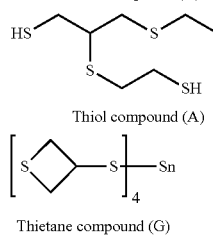

Thiol compound (A)

Thietane compound (G)

As clear from Table 7, it was found that the refractive indexes of Examples 23 to 25 were rather higher than that of Comparative Example 6. Example 1 in Table 7 refers to the product (desired product) obtained in Example 1.

Incidentally, in the above respective Examples, as a compound having at least two thiol groups in a molecule, there is used 4-mercaptomethyl-1,8-dimercapto-3,6-dithiaoctane. However, even when other polythiol compound (for example, 1,2,3-propanetrithiol, 2,5-dimercapto-1,4-dithiane, 5,7-dimercaptomethyl-1,11-dimercapto-3,6,9-trithiaundecane, 4,7-dimercaptomethyl-1,11-dimercapto-3,6,9-trithiaundecane, 4,8-dimercaptomethyl-1,11-dimercapto-3,6,9-trithiaundecane, 1,1,3,3-tetrakis(mercaptomethylthio)propane, 4,6-bis(mercaptomethylthio)-1,3-dithiane or 2-(2,2-bis(mercaptomethylthio)ethyl)-1,3-dithietane) is used, the same effects can be achieved.

The invention claimed is:

1. A composition comprising a product having a thiol group obtained by reacting an Sb or Bi oxide or an Sb or Bi halide with at least one kind of polythiol compounds selected from the group consisting of 1,2,3-propanetrithiol, 2,5-dimercapto-1,4-dithiane, 4-mercaptomethyl-1,8-dimercapto-3,6-dithiaoctane, 5,7-dimercaptomethyl-1,11-dimercapto-3,6,9-trithiaundecane, 4,7-dimercaptomethyl-1,11-dimercapto-3,6,9-trithiaundecane, 4,8-dimercaptomethyl-1,11-dimercapto-3,6,9-trithiaundecane, 1,1,3,3-tetrakis(mercaptomethylthio)propane, 4,6-bis(mercaptomethylthio)-1,3-dithiane and 2-(2,2-bis(mercaptomethylthio)ethyl)-1,3-dithietane, wherein the composition is capable of forming a transparent resin.

2. The composition as set forth in claim 1, wherein said polythiol compound is only composed of a carbon atom, a hydrogen atom and a sulfur atom.

3. The composition as set forth in claim 1, wherein said polythiol compound is 4-mercaptomethyl-1,8-dimercapto-3,6-dithiaoctane.

4. A polymerizable composition comprising the composition as set forth in claim 1, and at least one kind of compounds selected from the group consisting of an iso(thio)cyanate compound, an active hydrogen compound, an epoxy compound, an epithio compound and a thietane compound.

5. A resin obtained by polymerizing the polymerizable composition as set forth in claim 4.

6. An optical component comprising the resin as set forth in claim 5.

7. A method for producing a composition comprising a product having a thiol group synthesized by reacting an Sb or Bi oxide or an Sb or Bi halide with at least one kind of polythiol compounds selected from the group consisting of 1,2,3-propanetrithiol, 2,5-dimercapto-1,4-dithiane, 4-mercaptomethyl-1,8-dimercapto-3,6-dithiaoctane, 5,7-dimercaptomethyl-1,11-dimercapto-3,6,9-trithiaundecane, 4,7-dimercaptomethyl-1,11-dimercapto-3,6,9-trithiaundecane, 4,8-dimercaptomethyl-1,11-dimercapto-3,6,9-trithiaundecane, 1,1,3,3-tetrakis(mercaptomethylthio)propane, 4,6-bis(mercaptomethylthio)-1,3-dithiane and 2-(2,2-bis(mercaptomethylthio)ethyl)-1,3-dithietane, wherein the composition is capable of forming a transparent resin.

8. A polymerizable composition comprising the composition as set forth in claim 2, and at least one kind of compounds selected from the group consisting of an iso(thio)cyanate compound, an active hydrogen compound, an epoxy compound, an epithio compound and a thietane compound.

9. A resin obtained by polymerizing the polymerizable composition as set forth in claim 8.

10. An optical component comprising the resin as set forth in claim 9.

11. A polymerizable composition comprising the composition as set forth in claim 1, and at least one kind of compounds selected from the group consisting of an iso(thio)cyanate compound, an active hydrogen compound, an epoxy compound, an epithio compound and a thietane compound.

12. A resin obtained by polymerizing the polymerizable composition as set forth in claim 11.

13. An optical component comprising the resin as set forth in claim 12.

14. A polymerizable composition comprising the composition as set forth in claim 3, and at least one kind of compounds selected from the group consisting of an iso(thio)cyanate compound, an active hydrogen compound, an epoxy compound, an epithio compound and a thietane compound.

15. A resin obtained by polymerizing the polymerizable composition as set forth in claim 14.

16. An optical component comprising the resin as set forth in claim 15.

* * * * *